United States Patent
Taylor et al.

(10) Patent No.: US 6,530,875 B1
(45) Date of Patent: Mar. 11, 2003

(54) BRACHYTHERAPY SEED DEPLOYMENT SYSTEM

(75) Inventors: John Taylor, Trabuco Canyon, CA (US); Michael J. Ko, Mission Viejo, CA (US); Bruno J. Schmidt, Roseville, MN (US); Charles Beuchat, Irvine, CA (US)

(73) Assignee: Imagyn Medical Technologies, Inc., Irvine, CA (US)

( * ) Notice: Subject to any disclaimer, the term of this patent is extended or adjusted under 35 U.S.C. 154(b) by 0 days.

(21) Appl. No.: 09/694,107

(22) Filed: Oct. 20, 2000

(51) Int. Cl.[7] ............................. A61M 36/00; A61M 5/00
(52) U.S. Cl. ............................................ 600/7
(58) Field of Search .................... 600/1, 2, 3, 4, 600/5, 6, 7, 8, 564, 566; 604/57, 59, 60, 61; 250/507.1, 506.1; 976/DIG. 350

(56) References Cited

U.S. PATENT DOCUMENTS

| | | | |
|---|---|---|---|
| 5,928,130 A | | 7/1999 | Schmidt |
| 5,938,583 A | * | 8/1999 | Grimm ........................ 600/1 |
| 6,210,315 B1 | * | 4/2001 | Andrews et al. .............. 600/3 |
| 6,221,003 B1 | | 4/2001 | Sierocuk et al. |
| 6,245,052 B1 | | 6/2001 | Orth et al. |
| 6,264,599 B1 | * | 7/2001 | Slater et al. ................. 600/7 |
| 6,270,472 B1 | * | 8/2001 | Antaki et al. ................ 600/7 |
| 6,287,249 B1 | * | 9/2001 | Tam et al. .................... 600/3 |

* cited by examiner

*Primary Examiner*—Kevin Shaver
*Assistant Examiner*—Brian Szmal
(74) *Attorney, Agent, or Firm*—Knobbe, Martens, Olson & Bear, LLP

(57) ABSTRACT

Disclosed is a brachytherapy seed deployment system, for use in any of a variety of medical procedures such as radiation treatment of the prostate gland. The system includes a number of brachytherapy seed deployment needles, each preloaded with brachytherapy seeds in patterns and activities predetermined for a unique patient. The seeds are contained in transparent tubular sleeves, thereby allowing direct visualization of the brachytherapy seeds and spacers, so that the seed pattern may be inspected at the clinical site. A releasable retainer prevents accidental brachytherapy seed loss. The system additionally includes shipping containers, separately accessible calibration seeds and a display stand for use at the clinical site. Methods are also disclosed.

16 Claims, 19 Drawing Sheets

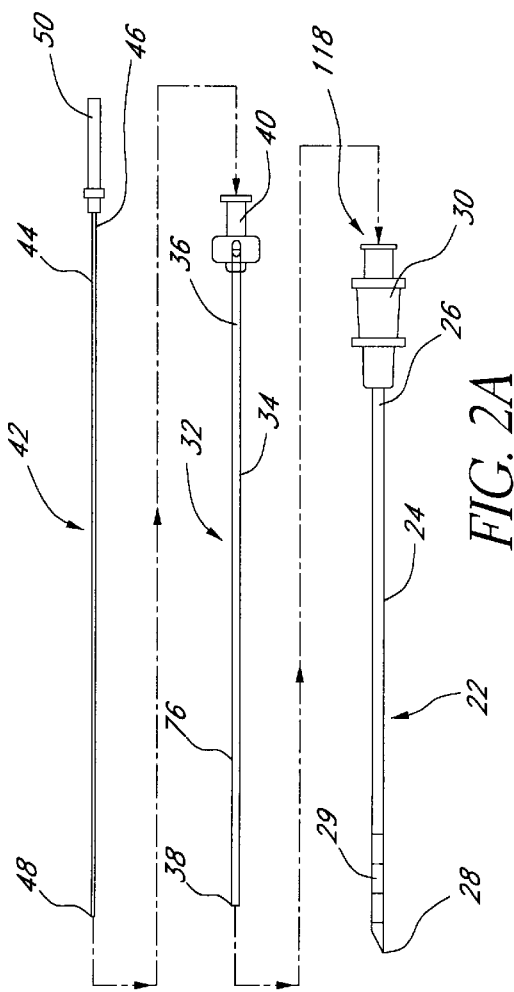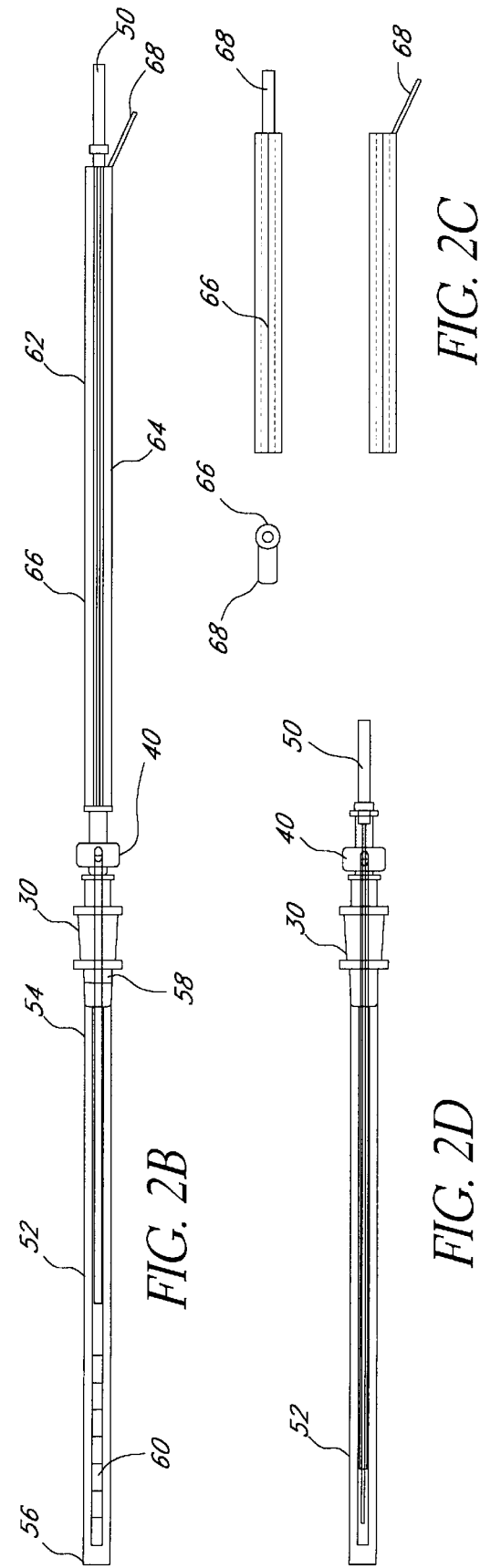

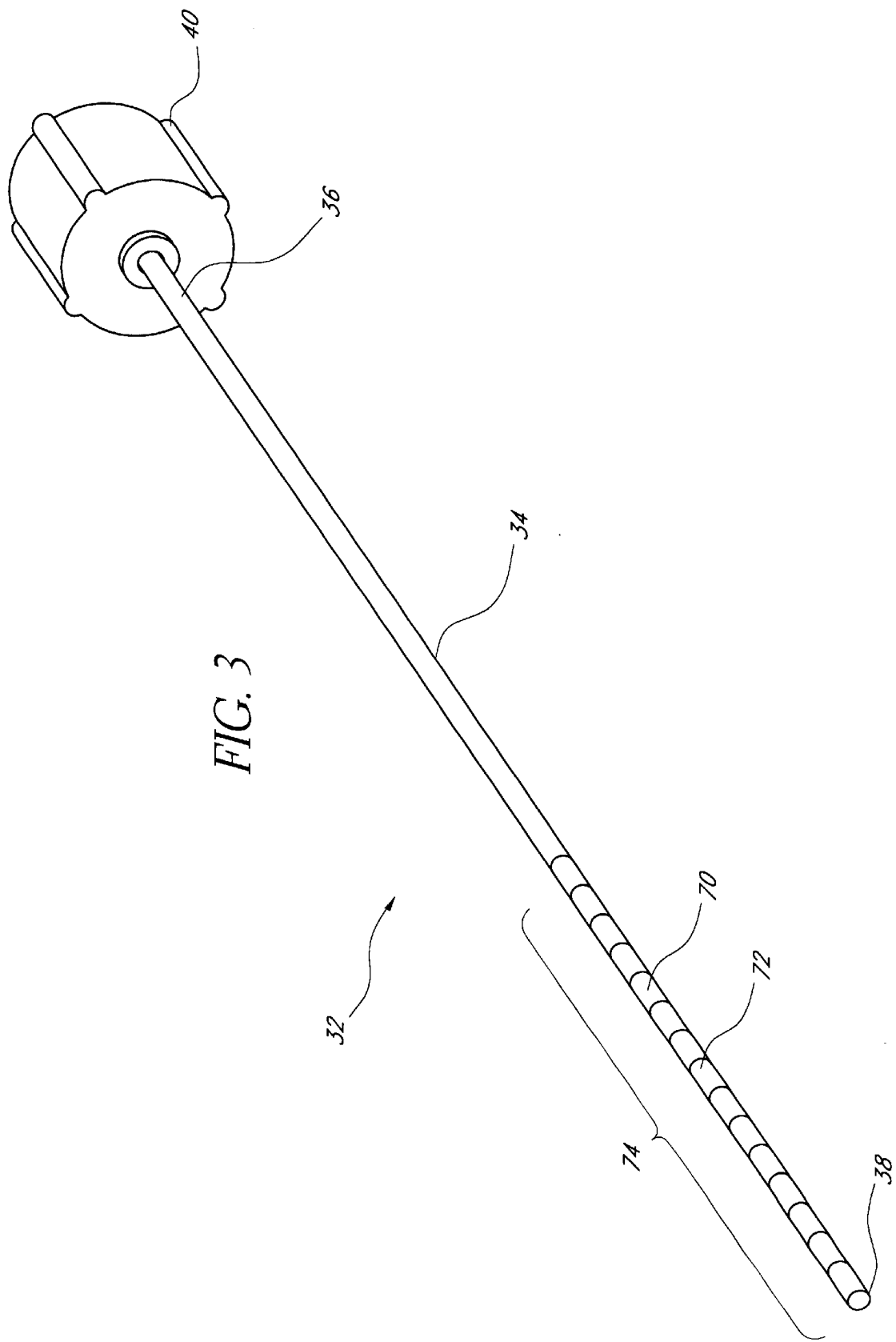

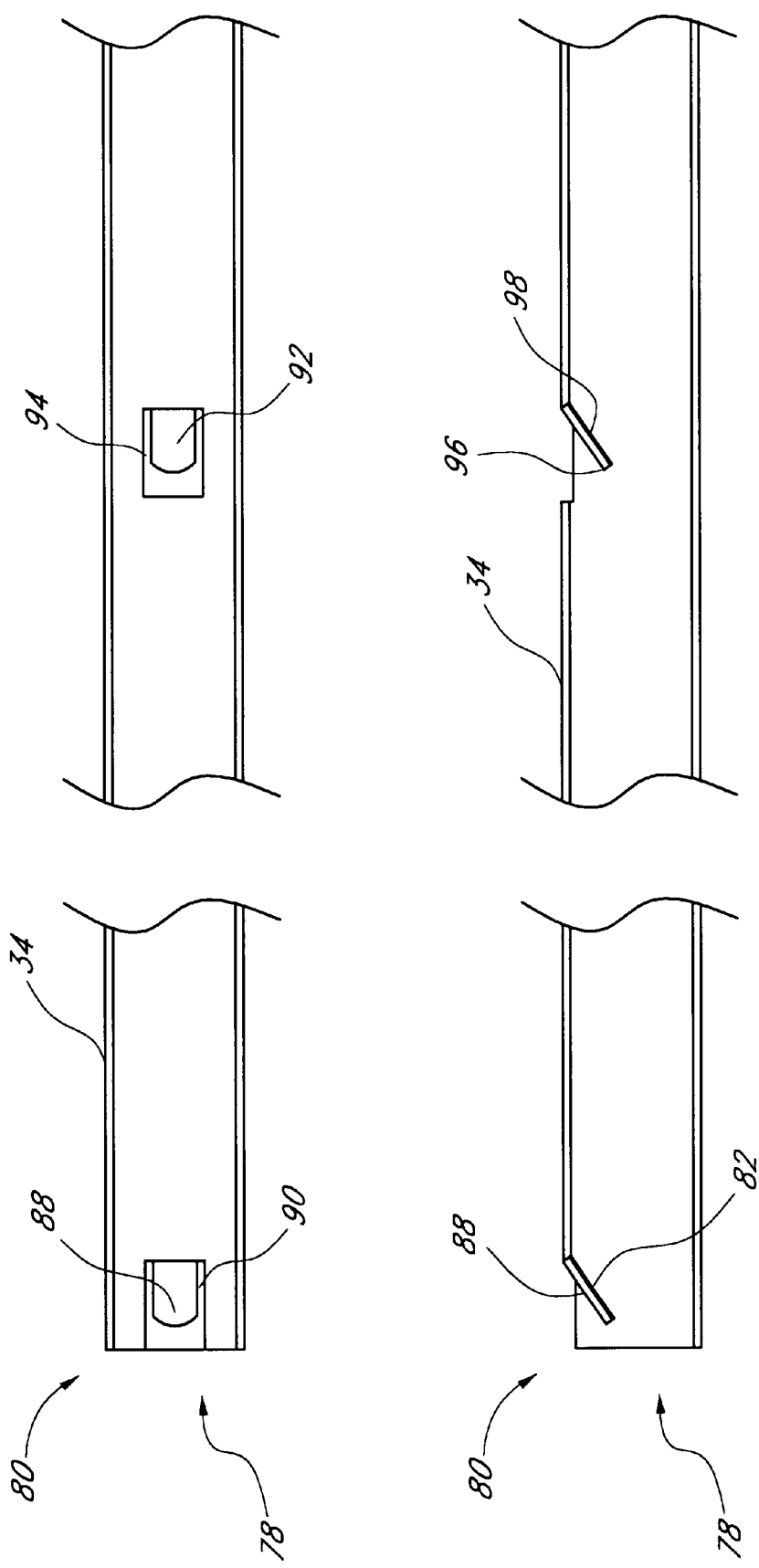

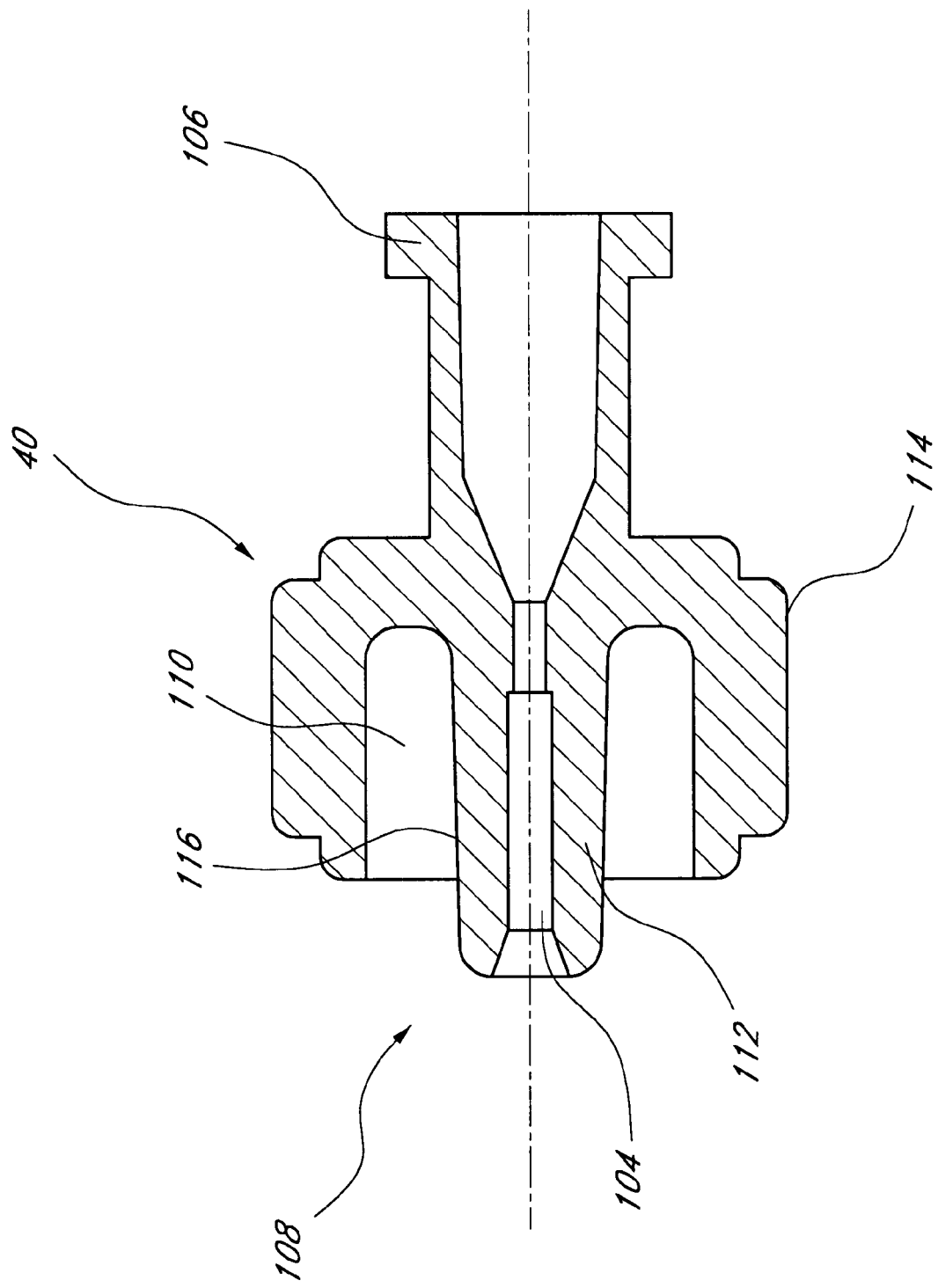

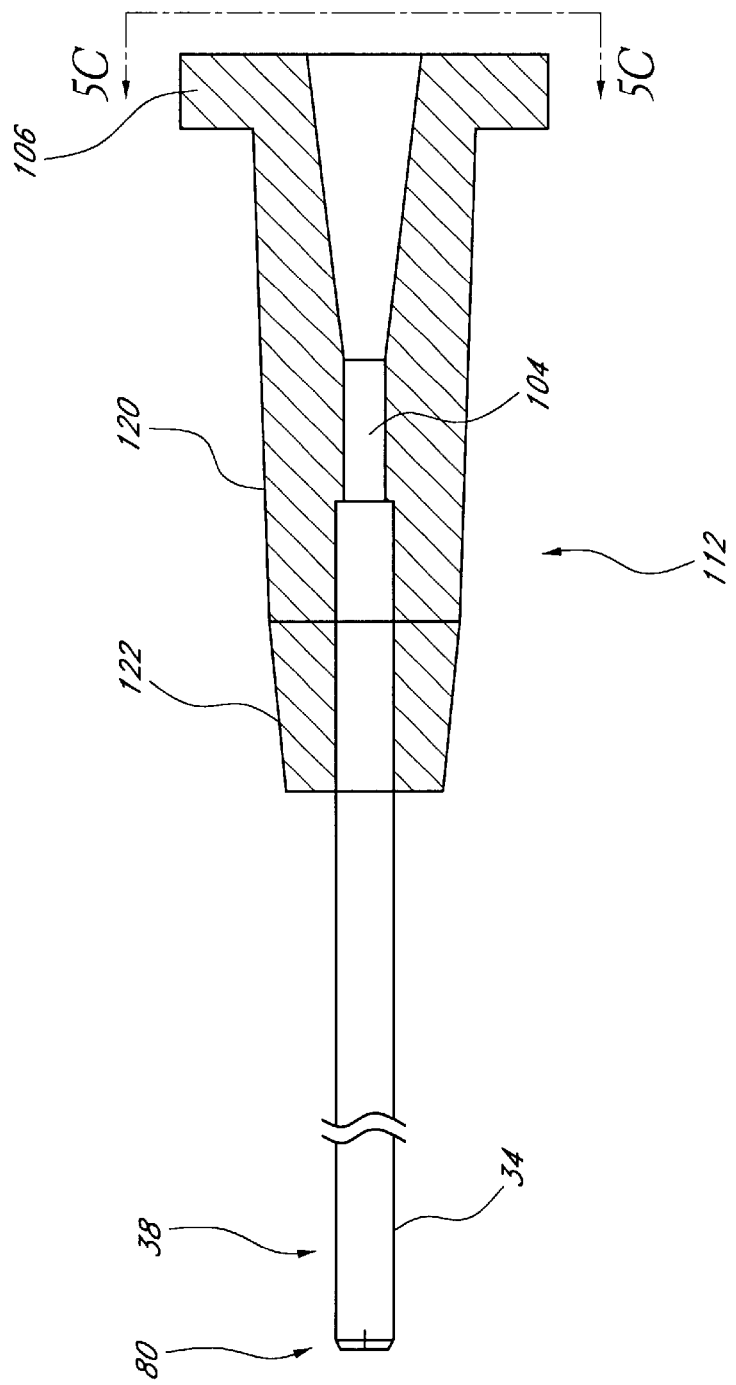

VariSeed: Needle Loading Report (Page 1)
VariSeed 6.7 (Build 1155) Seed Plan Pro 478-1 08/10/2000 10:31:52am

| Demo Studies, RRID #Demo | Study: Pre Operative Plan<br>Variation: Default<br>#Scars: 9<br>Template: B & K Standard | Isotope: I-125 (6711) 1999 c<br># Seeds: 92<br>Target Dose: 145.000<br>Anisotropic Correction: 0.930 | U/mCi: 1.270<br>U/Seed: 0.414<br>mCi/Seed: 0.326 |
|---|---|---|---|

| Needle Number | Retraction (cm) | Hole Location | Number Seeds |
|---|---|---|---|
| 1 | 0.00 | c4.0 | 5 |
| 2 | 0.00 | d4.0 | 5 |
| 3 | 0.50 | C3.5 | 4 |
| 4 | 0.50 | E3.5 | 4 |
| 5 | 0.00 | b3.0 | 5 |
| 6 | 0.00 | c3.0 | 2 |
| 7 | 0.00 | d3.0 | 2 |
| 8 | 0.00 | e3.0 | 5 |
| 9 | 0.50 | B2.5 | 3 |
| 10 | 0.50 | F2.5 | 3 |
| 11 | 1.00 | a2.0 | 2 |
| 12 | 0.00 | b2.0 | 5 |
| 13 | 0.00 | c2.0 | 5 |
| 14 | 0.00 | d2.0 | 5 |
| 15 | 0.00 | e2.0 | 5 |
| 16 | 1.00 | f2.0 | 2 |
| 17 | 0.50 | B1.5 | 3 |
| 18 | 0.50 | F1.5 | 3 |
| 19 | 1.00 | a1.0 | 2 |
| 20 | 0.00 | b1.0 | 5 |
| 21 | 0.00 | c1.0 | 5 |
| 22 | 0.00 | d1.0 | 5 |
| 23 | 0.00 | e1.0 | 5 |
| 24 | 1.00 | f1.0 | 2 |

● =Special loading

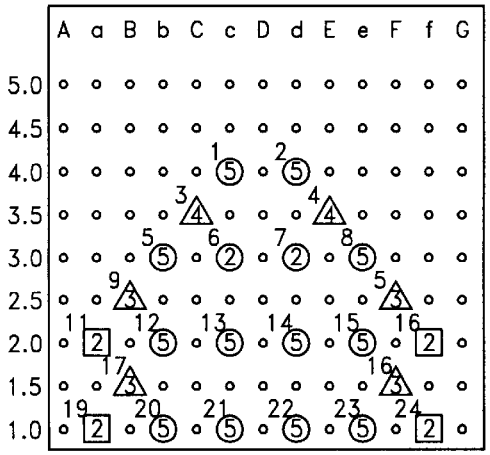

| Retraction Legend | | | | | |
|---|---|---|---|---|---|
| Plane 0 | Plane 1 | Plane 2 | Plane 3 | Plane 4 | special |
| 0.00cm | 0.50cm | 1.00cm | 1.50cm | 2.00cm | other |
| ○ | △ | □ | ◇ | ▽ | ○ |

| Number of Needles | Seeds per Needle |
|---|---|
| 6 | 2 |
| 4 | 3 |
| 2 | 4 |
| 12 | 5 |

| Plan Summary | |
|---|---|
| Total Activity [U] | 38.09 |
| Total Activity [mCi] | 29.99 |
| Total Needles | 24 |
| Total Seeds | 92 |
| Extra Seeds | |
| Total Seeds to Order | |

FIG.7A

Study Created by _____
Study Approved by _____

VariSeed: Needle Loading Report (Page 1)
VariSeed 6.7 (Build 1155) Seed Plan Pro 478-1 08/10/2000 10:31:52am

| Demo Studies, RRID #Demo | Study: Pre Operative Plan<br>Variation: Default<br>#Scans: 9<br>Template: B & K Standard |
|---|---|

| Needle Number | Retraction (cm) | Hole Location | Number Seeds |
|---|---|---|---|
| 1 | 0.00 | c4.0 | 5 |
| 2 | 0.00 | d4.0 | 5 |
| 3 | 0.50 | C3.5 | 4 |
| 4 | 0.50 | E3.5 | 4 |
| 5 | 0.00 | b3.0 | 5 |
| ● 6 | 0.00 | c3.0 | 2 |
| ● 7 | 0.00 | d3.0 | 2 |
| 8 | 0.00 | e3.0 | 5 |
| 9 | 0.50 | B2.5 | 3 |
| 10 | 0.50 | F2.5 | 3 |
| 11 | 1.00 | a2.0 | 2 |
| 12 | 0.00 | b2.0 | 5 |
| 13 | 0.00 | c2.0 | 5 |
| 14 | 0.00 | d2.0 | 5 |
| 15 | 0.00 | e2.0 | 5 |
| 16 | 1.00 | f2.0 | 2 |
| 17 | 0.50 | B1.5 | 3 |
| 18 | 0.50 | F1.5 | 3 |
| 19 | 1.00 | a1.0 | 2 |
| 20 | 0.00 | b1.0 | 5 |
| 21 | 0.00 | c1.0 | 5 |
| 22 | 0.00 | d1.0 | 5 |
| 23 | 0.00 | e1.0 | 5 |
| 24 | 1.00 | f1.0 | 2 |
| ● =Special loading | | | |

*FIG. 7B-1*

| FIG.7B-1 | FIG.7B-2 |
|---|---|

*FIG. 7B*

BRACHYTHERAPY SEED DEPLOYMENT SYSTEM

BACKGROUND OF THE INVENTION

This invention relates to the field of brachytherapy and the manufacture and handling of small radioactive seeds. Brachytherapy involves the implantation of small radioactive seed, or pellets into tumors to eradicate cancerous cells, and is an alternative to external radiation therapy such as electron beam irradiation.

Brachytherapy has been used in the treatment of numerous types of cancer, including cervical, breast, lung, head and neck, and prostate. As an example of the procedure the treatment of prostate cancer will be used. This is in no way intended to limit the scope of this application, as the use of the invention disclosed herein has general application in the handling of the radioactive pellets, or seeds, as will be obvious to those skilled in the art.

The treatment of prostate cancer using radioactive seed implantation has been known for some time. Currently either Palladium-103 or Iodine-125 seeds are used, with apparent activities ranging from about 0.25 mcuries to 1.2 mcuries, depending on the prostate size and aggressiveness of the cancer. Recent advances in ultrasound imaging and other technological advancements have enabled this procedure to become a very viable alternative to other treatments such as external beam irradiation and radical prostatectomy. The procedure involves ultrasound mapping of the prostate gland and size of tumor using a transrectal ultrasound probe. A radiation oncologist will then decide on the number and positioning of the radioactive seeds needed to deliver a sufficient amount of radiation to kill the cancerous cells. The requisite number of radioactive seeds are typically loaded into 18 gauge brachytherapy needles. Needles may contain anywhere from one to seven seeds, usually separated by bio-absorbable spacers of catgut or other suitable suture material. To prevent the seeds and/or the spacers from falling out of the needle accidentally, the distal end of the needle, the tip, is plugged with a small amount of bone-wax. Bone-wax is a medical grade beeswax material. The seeds are prevented from falling out of the proximal or hub end of the needle by a blunt obturator, which is ultimately used to force the seeds from the 18 gauge needle once in position in the prostate. The needles are inserted into the prostate transperineally.

In a typical procedure the needles loaded with seeds are inserted into the prostate gland under the guidance of the ultrasound rectal probe. A metal grid, abutting the s peritoneum, having X-Y coordinates is matched to a grid overlaid on the real-time ultrasound picture, so that the requisite number of seeds can be placed at each location in accordance with the mapping planes used by the radiation oncologist to optimize dose delivery. Once the tip of the needle is visualized in the correct location on the ultrasound screen, the needle is withdrawn over the obturator whilst maintaining the position of the obturator, such that a pattern of seeds and spacers is laid down as required. Typically about 85 seeds are placed during the procedure, but the number can be as high as about 140 or as low as about 40. Thus a typical procedure uses about 30 needles per patient.

Currently the seeds and the spacers are loaded into the needles by the radiation oncologist or radiation physicist by hand. This is a laborious task, and can take up to an hour to complete. This can tie-up Operating Room time, and at a minimum is wasting radiation oncologist or physicist time. Furthermore, during this time the person doing the loading is exposed to undesirable levels of radiation, and the loading task is extremely fatiguing. Some mechanical assist devices exist, but they are either unreliable, and can jam or, even worse, break or crush a seed allowing radioactive material to escape. In addition, verification of seed loading per needle is generally not readily accomplished. A system marketed by Northwest Radiation Therapy Products organizes the seeds, spacers, and needles on a stand. This lessens operator movement, but the process is still time consuming.

An alternate approach for delivering the seeds to the patient is typified by instruments called the Mick Applicator and the Quick Seeder Applicator sold by Mick Radio-Nuclear Instruments, Inc. In this system the empty needles are first inserted into the patient at the predetermined locations. Then using the Mick Applicator one seed at a time is delivered from a pre-loaded cartridge, indexing back a pre-determined distance after delivering each individual seed. In the case of the Quick Seeder Applicator, a cartridge pre-loaded with seeds and spacers is attached to the needle. This device transfers a column of seeds and spacers by indexing back a pre-determined distance to accomplish the delivery. Again the cartridges are loaded either by hand or by using a device that consists of a chamber in which the seeds and spacers are lined up before being pushed into the cartridge. This is time consuming because seeds and spacers still have to be hand loaded into the transfer chamber, thus offering little benefit over straight hand loading. The invention described herein overcomes the deficiencies in the prior art and provides an improved means for loading needles. No supplier provides pre-loaded needles for brachytherapy.

U.S. Pat. No. 5,928,130 by Schmidt describes a tool for implanting radioactive seeds that includes a needle, spacers and seeds loaded into a transparent or translucent sleeve, and an obturator to facilitate the displacement of spacers and seeds and deposit them into tissue.

Notwithstanding the various efforts in the prior art, there remains a need for a preloaded brachytherapy seed system as described in detail below.

SUMMARY OF THE INVENTION

One aspect of the present invention is to enable brachytherapy needles to be preloaded with radioactive seeds and spacers, organized, packaged and shipped sterile in quantities prescribed on a per order basis. Another aspect of the invention is to provide one prescription in one shipper. Another aspect of the invention is to provide a system that allows for at least about 10% of the seeds to be assayed for activity without affecting the sterility of the pre-loaded seeds for implantation. Yet another aspect of the invention is to provide a system that allows for the addition of about two extra needles for insertion of extra seeds in order to accommodate unforeseen adjustments in the procedure.

Another aspect of the invention is to eliminate the preparation time at the clinical site of loading and sterilizing the seeds as required in the past. Yet another aspect is to reduce operator exposure to radiation to a minimum and to reduce Operating Room use, thus reducing costs. Another aspect of the present invention is to reduce the amount of paper work required by the hospital by reducing the invoicing, ordering and stocking from four individual products to one.

Another aspect of the invention is to provide a system that optimizes the needle layout by arranging the needles in order by needle number previously prescribed in the treatment plan. Yet another aspect of the invention is to provide a system that allows the user to remove any one of the needles at any time during the procedure and does not require that the needles be unloaded sequentially thus providing the physician with flexibility during the procedure without adding concern about potentially damaging the pre-loaded needles. Another aspect of the invention is to provide pre-loaded sleeves having a marker corresponding to the number of seeds in the sleeve. Another aspect of the invention is to provide pre-loaded sleeves identified with their corresponding needle numbers according to the pre-planned prescription information.

Another aspect of the invention is to provide a system that allows the loading pattern of each needle to be confirmed at any time up to and including the time of implant. The loading pattern is confirmed by removing the sleeve from the needle and viewing the seeds and spacers through the sleeve.

Yet another aspect of the invention is to provide a sterile system that eliminates the time and processing equipment needed to sterilize the components on site, thus reducing the cost. Another aspect of the invention is to provide a system that allows for double aseptic transfer of the injected components into the sterile field of the operating room.

Another aspect of the invention is to provide a system that allows the physician to implant seeds and spacers using their current method. Yet another aspect of the invention is to provide the physician with a tactile feedback of the dispensing of spacers and seeds, thus providing the user with a confirmation that spacers and seeds are being implanted.

The invention comprises a system of components that enable brachytherapy needles to be pre-loaded with radioactive seeds and spacers, organized, packaged and shipped sterile from the manufacturing facility to the clinical site in quantities prescribed on a per patient per order basis. In a preferred embodiment the seeds required for assay of the activity of the shipment are provided in a manner that does not compromise the sterility of the seeds for implantation. In a preferred embodiment additional extra empty needles are provided to accommodate unforeseen adjustments in the procedure that require insertion of extra seeds.

In a preferred embodiment, the seeds and spacers are loaded in transparent or translucent sleeves that allow visual confirmation of the loading pattern of seeds and spacers up to and including the time of implant. In a preferred embodiment the seeds and spacers are retained in the sleeve by a retaining element. In a preferred embodiment the system provides the physician with confirmation in the form of tactile feedback of the dispensing of each seed and each spacer.

In a preferred embodiment, the pre-loaded sleeves are marked with an indication of the number of seeds inside. In a preferred embodiment the pre-loaded sleeve is marked with an identifier indicating which corresponding needle it should be used with according to the pre-planned prescription information and treatment plan.

In a preferred embodiment the system allows for double aseptic transfer of the injected components into the sterile field of the operation room.

Thus, there is provided in accordance with one aspect of the present invention a brachytherapy seed and spacer deployment system, which includes a deployment device. The deployment device comprises an elongate tubular sleeve, having a proximal end and a distal end. An elongate obturator is axially movable through the tubular sleeve. At least one retention structure is provided on the tubular sleeve, for retaining brachytherapy seeds and spacers therein. The retention structure is movable between a first position in which it will retain a seed and spacer within the sleeve, and a second position in which it will release the seed and spacer separately from the sleeve.

Preferably, the retention structure is biased in the direction of the first position. The sleeve is also preferably visually transparent.

In one embodiment, the system further comprises a lock on the obturator, for resisting distal advancement of the obturator through the sleeve. The obturator lock may comprise a tubular wall, having an axially extending slot therein. The tubular wall surrounds a proximal portion of the obturator, which extends proximally from the tubular sleeve and prevents distal advancement of the obturator into the sleeve.

In accordance with another aspect of the present invention, there is provided a method of controllably deploying a plurality of seeds and spacers from a brachytherapy seed deployment device. The method comprises the steps of providing a brachytherapy seed deployment device, having a tubular body, a plurality of seeds and spacers therein, a deployment control, and a releasable retainer for preventing inadvertent release of seeds and spacers from the device. The device is positioned at a treatment site, and the control is manipulated to deploy a first seed past the retainer and from the device. The retainer is permitted to retain at least a spacer within the device. In one embodiment, the manipulating the control step comprises distally advancing an obturator. Preferably, the method further comprises the step of deploying at least a spacer past the retainer and from the device. In many applications, at least a second and often at least a third seed are controllably sequentially deployed.

In accordance with a further aspect of the present invention, there is provided a brachytherapy system. The system comprises an elongate tubular needle, and an elongate tubular sleeve positioned within the needle. The sleeve has a proximal end and a distal end. At least one brachytherapy seed is positioned in the sleeve, and an obturator extends into the proximal end of the sleeve. The needle is carried by a flexible drape. Preferably, a plurality of brachytherapy seeds and spacers are positioned within the sleeve. In addition, a plurality of needles are preferably carried by the drape.

The foregoing drape carrying a plurality of needles may be positioned within a needle pig. The system preferably additionally comprises one or more calibration seeds. The calibration seeds are preferably carried by a calibration seed pig, or carried in a calibration seed cavity on the needle pig, such that the calibration seeds can be accessed without exposing the needles.

In accordance with another aspect of the present invention, there is a provided a brachytherapy system. The brachytherapy system comprises a shipping container, having a needle pig carried therein. A calibration seed pig is also provided in the shipping container. A plurality of brachytherapy needles are positioned in the needle pig, the brachytherapy needles preloaded with brachytherapy seeds and spacers. At least one, and in some embodiments a plurality of calibration seeds are provided in the calibration pig, such that the calibration seed or seeds can be accessed without opening the needle pig.

Preferably, the brachytherapy needles are carried by a flexible drape. The system preferably additionally comprises a needle loading report, for identifying the contents of each needle and the target position for each needle in the patient.

In accordance with another aspect of the present invention, there is provided a nonuniform dosing profile brachytherapy needle set. The needle set comprises a flexible drape, and a plurality of needles, each containing at least one brachytherapy seed, the needles carried by the drape. At least a first seed in a first needle is provided with a first activity, and at least a second seed in a second is provided with a second, different activity. In one embodiment, at least a third seed having a third activity is positioned in the first needle.

In accordance with another aspect of the present invention, there is provided a nonuniform dosing profile brachytherapy seed deployment device. The device comprises a brachytherapy needle, and a tubular sleeve within the needle. A plurality of brachytherapy seeds and spacers are positioned within the sleeve, such that the device exhibits a first activity in a first zone and a second activity in a second zone.

In accordance with further aspects of the present invention, there are provided methods for customizing a dosing profile to the three-dimensional target tissue within a patient. The method comprises the steps of identifying the three-dimensional shape of the target tissue within a patient, and preloading a plurality of brachytherapy seeds having two or more activities into a plurality of brachytherapy needles in a pattern which corresponds to the three-dimensional profile of the target tissue. The brachytherapy needles are labeled and delivered to the clinical site. Each needle is thereafter inserted into its predetermined location within the target tissue, to reconstruct the predetermined three-dimensional dosing profile for that patient.

Further features and advantages of the present invention will become apparent to those of skill in the art in view of the detailed description of preferred embodiments which follows, when considered together with the attached drawings and claims.

BRIEF DESCRIPTION OF THE DRAWINGS

The novel features, advantages, and aspects of the present invention will be more readily understood upon reading the following detailed description taken in connection with the accompanying drawings in which:

FIG. 2A is a schematic exploded view of components of the invention;

FIG. 2B is a side elevational view of an assembled, loaded deployment device in accordance with the present invention;

FIG. 2C are schematic views of an obturator lock in accordance with the present invention;

FIG. 2D is a side elevational view as in FIG. 2B, without brachytherapy seeds and with the obturator fully distally advanced;

FIG. 3 is a front perspective view of a sleeve assembly pre-loaded with seeds and spacers;

FIGS. 4A, 4B, 4C and 4D are views of seed and spacer retaining elements;

FIG. 5A is a cross-sectional view of a sleeve hub;

FIG. 5B is a cross-sectional view of an alternate sleeve hub;

FIG. 5C is an end view of the sleeve hub of FIG. 5B.

FIGS. 7A and 7B are a needle loading report;

DETAILED DESCRIPTION OF PREFERRED EMBODIMENTS

Figure 1:
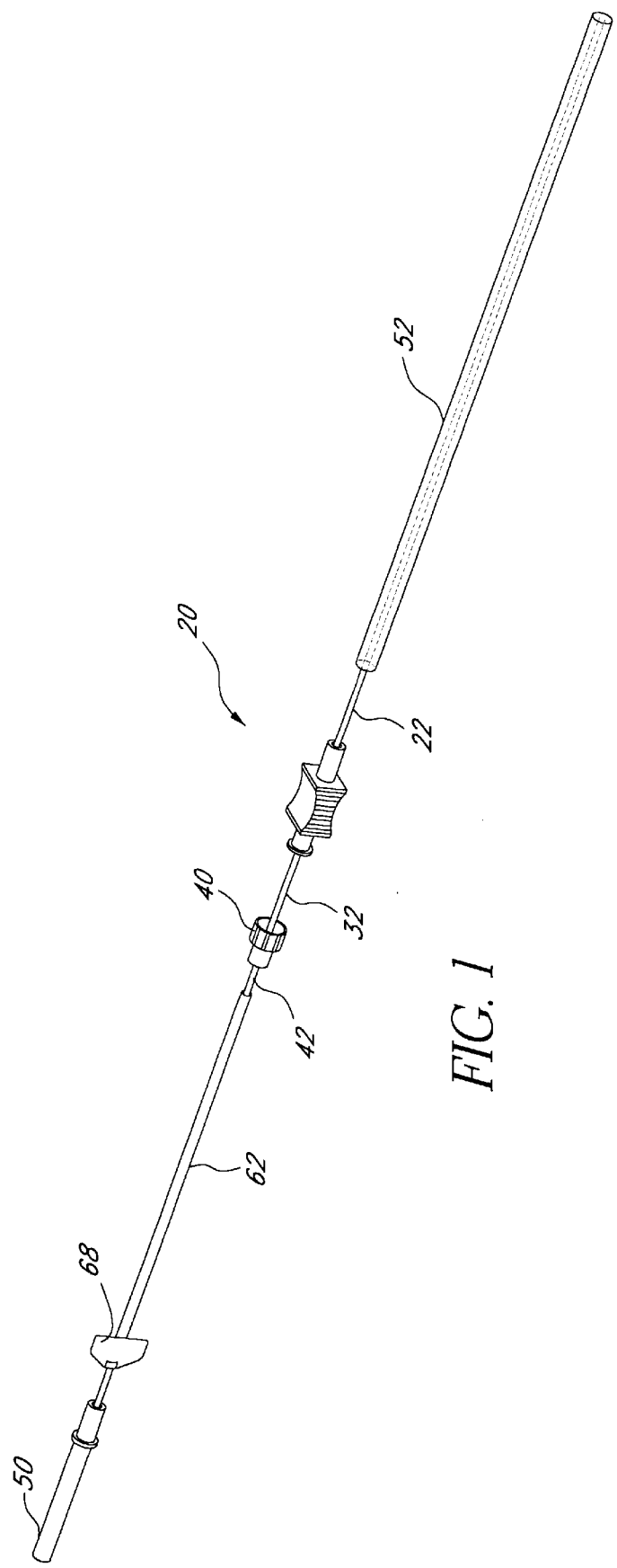
FIG. 1 is a partially exploded perspective view of components of the invention.
Figures 2, 7B:
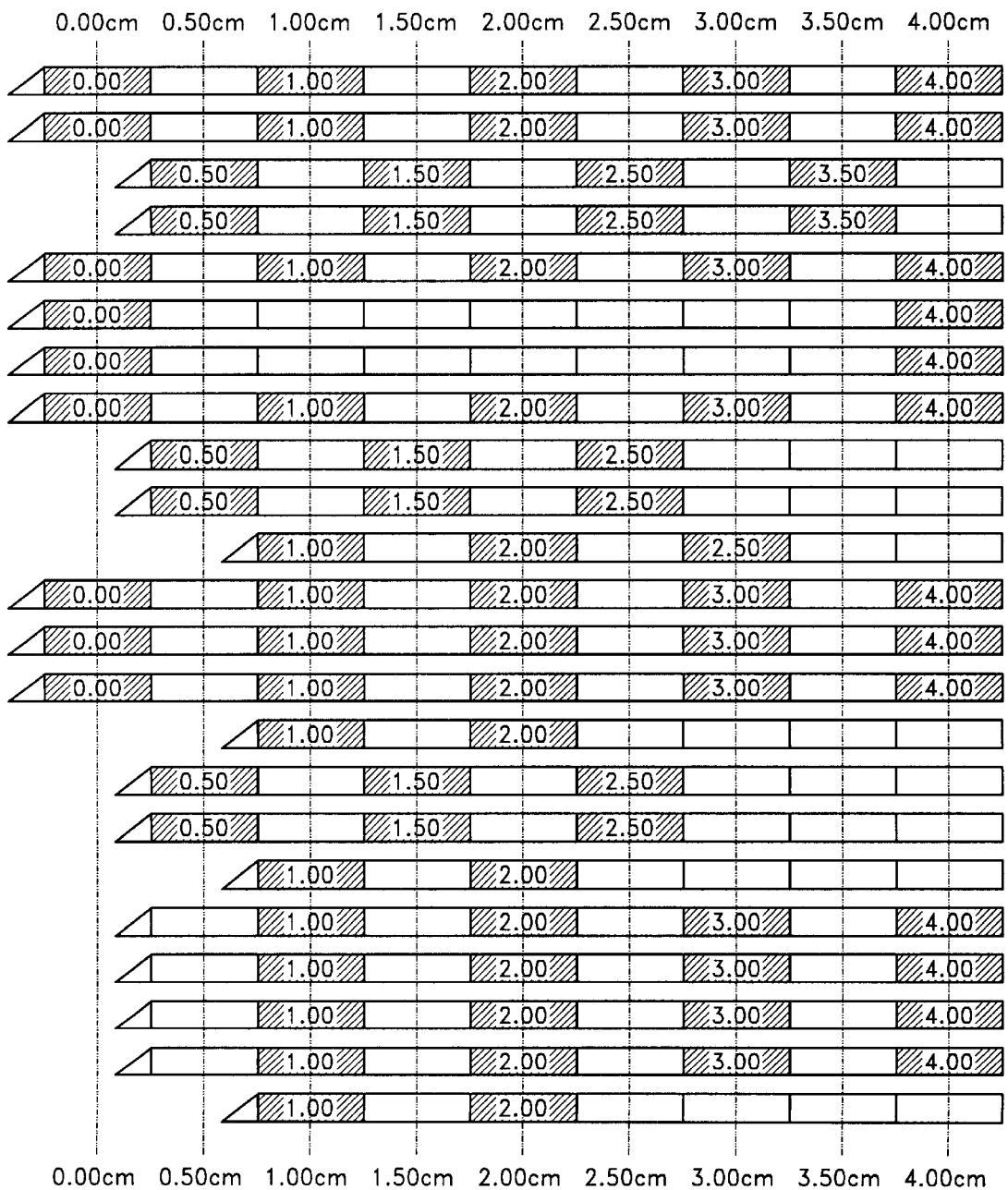

Referring to FIGS. 1 through 3, there is illustrated a brachytherapy seed deployment device 20 in accordance with one aspect of the present invention. The deployment device 20 is adapted to controllably deploy a plurality of radioactive seeds and spacers along a linear path in a target tissue site. Radioactive seeds and spacers may be individually deployed, with tactile feedback to the operator as each seed and spacer leaves the device. The risk of inadvertent deployment or loss of radioactive seeds or spacers is minimized or reduced by the distal tip design as will be discussed below.

The deployment device 20 comprises an elongate needle 22 for penetrating tissue to reach the target site as is known in the art. Needle 22 comprises an elongate tubular body 24 extending between a proximal end 26 and a sharpened distal tip 28 for puncturing tissue. See FIG. 2A. Proximal end 26 is provided with a Hub 30 as is understood in the art. In general, needle 22 has an axial length which is sufficient to reach the target tissue, from a predetermined access point. Thus, depending upon the target and access point, various needle lengths may be utilized. Axial lengths within the range from about 6 inches to about 12 inches and, in one embodiment, about 7.9 inches, are utilized in a system intended to treat the prostate gland.

Needles of various diameters may also be utilized, with an optimum diameter for any particular application selected to be sufficient to carry an appropriate seed while minimizing the cross-section of the puncture. In a system intended for treating the prostate gland, needles within the range from about 26 gauge to about 12 gauge, and, in one embodiment, 18 gauge, will normally be used. Needles made from any of a variety of materials including stainless steel, nitinol, or others may be utilized as will be understood in the art.

Tubular sleeve 32 is dimensioned to be axially slidably positioned within the needle 22. Sleeve 32 comprises an elongate tubular body 34, extending between a proximal end 36 and a distal end 38. Proximal end 36 is provided with a Hub 40. The distal end 38 of sleeve 32 is preferably provided with one or more brachytherapy seed retention structures, which will be disclosed in greater detail below.

Sleeve 32 is adapted to slidably receive one or more radioactive seeds for deployment at a tissue site. Generally, from one to about seven seeds, usually separated by bioabsorbable spacers of cat gut or other suitable material will be preloaded into the sleeve depending upon the particular clinical needs of the patient. The preloading process preferably occurs at the point of manufacture or at a loading station which is remote from the clinical site.

Tubular body 34 is preferably manufactured from a material which permits visual observation of the contents, so that the physician or other clinical staff may observe the number and location of seeds and spacers within the sleeve 32.

Materials having sufficient structural integrity and transparency for this purpose can be readily determined through routine experimentation by those of skill in the art in view of the objectives recited herein. In one embodiment, intended for use with an 18 gauge needle, tubular body 34 comprises a polyimide extrusion having an outside diameter of about 0.039 inches, an inside diameter of about 0.036 inches and a wall thickness of about 0.0015 inches. The specific dimensions of the sleeve 32 will be determined to cooperate with the Needle 22 as will be apparent to those of skill in the art in view of the disclosure herein.

An obturator 42 is adapted to be axially slidably received within the sleeve 32. Obturator 42 comprises an elongate body 44 having a proximal end 46 and a distal end 48. A Hub or control 50 is provided at the proximal end 46. The body 44 may comprise either a solid rod or a tubular element. Solid rods or tubes of stainless steel or other medically acceptable metals may be utilized. Alternatively, extruded rod or tubing of a polymeric material may also be utilized. In one embodiment, the body 44 comprises ABS plastic. The outside diameter of the body 44 is adapted to be slidably received within the sleeve 32. Thus, in a system adapted for use with an 18 gauge needle, and a sleeve 32 having an inside diameter of about 0.036 inches, the outside diameter of body 44 of Obturator 42 is about 0.032 inches.

The role of the obturator 42 is to distally advance the seeds 70 and spacers 72 from the distal end 38 of the sleeve 32. As a consequence, distal end 48 of obturator 42 is preferably blunt, and provided with as large a cross-sectional area as will be slidably accommodated within the sleeve 32. Slidability may be optimized by providing the distal end 48 with a slight chamfer or break to reduce snagging. The axial length of the obturator 42 is preferably sufficient that the distal end 48 will reach the distal end 38 of the sleeve 32 at or about the time the Hub 50 engages Hub 40. In this manner, the entire contents of the sleeve 32 may be deployed into the patient.

Referring to FIG. 2B, the foregoing elements are illustrated in a loaded and locked orientation, such as for shipping and handling. The sleeve 32 carries a deployable load 60 such as a plurality of radioactive seeds 70 and spacers 72. Sleeve 32 is positioned within Needle 22, and obturator 42 is advanced distally through the central lumen 76 of sleeve 32 to about the point of contact with the proximal end of the deployable load 60.

The loaded needle and sleeve assembly is coaxially positioned within an outer needle shield 52. Needle shield 52 preferably extends between a proximal end 54 and a distal end 56. The axial length of the needle shield 52 is preferably longer than the axial length of the Needle 22, to minimize the risk of needle sticks during handling. The proximal end 54 of needle shield 52 is preferably frictionally engaged with the Hub 30, such as at a distal tapered engagement surface 58. Needle shield 52 may be removed at the clinical site, to expose the distal tip 28 of the Needle 22 for insertion at the treatment site.

In one embodiment in which needle 22 extends approximately 7.9 inches distally of the hub 30, needle shield 52 has an axial length of about 8.25 inches. The inside diameter of the needle shield 52 is sufficient to slidably receive needle 22 axially therethrough. In one embodiment intended for use with an 18 gauge needle, the needle shield 52 has an inside diameter of about 0.16 inches and an outside diameter of about 0.20 inches. Needle shield 52 may be manufactured by any of a variety of techniques well known in the art, such as extrusion of any of a variety of polymers well known in the medical device arts.

The deployment device 20 is further illustrated with an obturator lock 62. See FIG. 2B. In the loaded configuration, the proximal end 46 of the obturator 42 is positioned proximally of the hub 40 of sleeve 32 by a distance which corresponds to the axial length of the deployable load 60. Distal advancement of the obturator hub 50 will deploy the deployable load 60 out of the distal end 38 of the sleeve and distal tip 28 of the needle 22. Premature advancement of the hub 50, such as during handling or positioning of the needle 22, may accidentally deploy a portion or all of the deployable load 60 prior to the time that the needle 22 is appropriately positioned at the treatment site. In many radiation treatments, particularly in the prostate gland, a large number of needles 22 will be loaded with unique patterns or numbers of radioactive seeds. As a consequence, inadvertent loss of radioactive seeds from the sleeve 32 can significantly complicate and delay the procedure while the unique pattern of seeds and spacers for that needle is reconstructed. In addition, the possibility of accidental deployment of radioactive seeds in the operating room is disadvantageous to the clinical staff.

The present invention thus provides a lock for resisting distal advancement of the obturator 42 until the desired deployment time. Lock 62 thus axially fixes the position of the obturator 42 with respect to the hub 30, until the lock is released. This lock may be accomplished using any of a variety of structures, such as Toohey-Borst type hubs, clamps, cams or other friction generating structures at about the hub 30. Alternatively, as illustrated in FIG. 2B, the obturator lock 62 comprises an elongate axial support, such as a tubular body 64, which is dimensioned to extend coaxially around the obturator 42, but not around the hub 30 or hub 50. In this manner, hub 50 cannot be advanced distally towards hub 30 until the obturator lock 62 has been removed. Obturator lock 62 in the illustrated embodiment comprises a tubular body 64 having an axially extending longitudinal slit 66 to allow the obturator lock 62 to be advanced laterally onto and removed from the obturator 42. A pull tab 68 may be provided on the tubular body 64, preferably centered approximately 180° apart from the longitudinal slit 66. The pull tab 68 may be pulled away from the obturator 42, thereby causing the tubular body 64 to be peeled away from the obturator 42. This low profile, low cost locking structure enables the positioning of the brachytherapy seed deployment device 20 at the treatment site, and then rapid removal of the obturator lock 62 by pulling pull tab 68 when the time is appropriate to deploy the deployable load 60.

Although the present invention is described primarily herein in the context of the radiation delivery device, it will be understood by those of skill in the art that the deployable load 60 may comprise any of a variety of devices, structures, or materials that may desirably be implanted within the body. For example, any of a wide variety of medications may be included within the sleeve 32. Drugs in solid or liquid form, time release structures, such as microporous materials or gels, or prosthetic devices may alternatively be deployed from the system disclosed herein.

Referring to FIG. 2D, the deployment system of FIG. 2B is illustrated, with the obturator lock 62 removed, and the obturator hub 50 advanced to its distal limit of travel in contact with the hub 40.

The obturator lock 62 may be manufactured in any of a variety of ways, which are known in the art. For example, obturator lock 62 may be extruded in tubular form, with the longitudinal slit 66 and tab 68 formed as a post-extrusion step. Materials such as various densities of polyethylene, polyethylene terephthalate, nylon, PEBAX, or others well known in the catheter and medical device arts may be utilized. In one embodiment, the obturator lock 62 comprises an extruded polypropylene tube having an inside diameter of about 0.06 inches, an outside diameter of about 0.09 inches, and an axial length of about 3.3 inches.

Preferably, the needle 22 is provided with markings along its axial length to allow visual observation of the depth of penetration at the treatment site. In addition, a distal zone 29 is preferably provided with a textured surface or radiopaque coating to enhance visualization as will be understood in the art.

Referring to FIG. 3, the tubular body 34 is illustrated with a load of seeds 70 and spacers 72. The seeds 70 and spacers 72 together define a deployable load length 74. The length 74 will vary depending upon the clinical needs of the patient. In general, load lengths within the range of from about 0.30 inches to about 3.31 inches are utilized in most applications where the device is utilized to deliver radioactive seeds to the prostate gland.

Figure 4A:
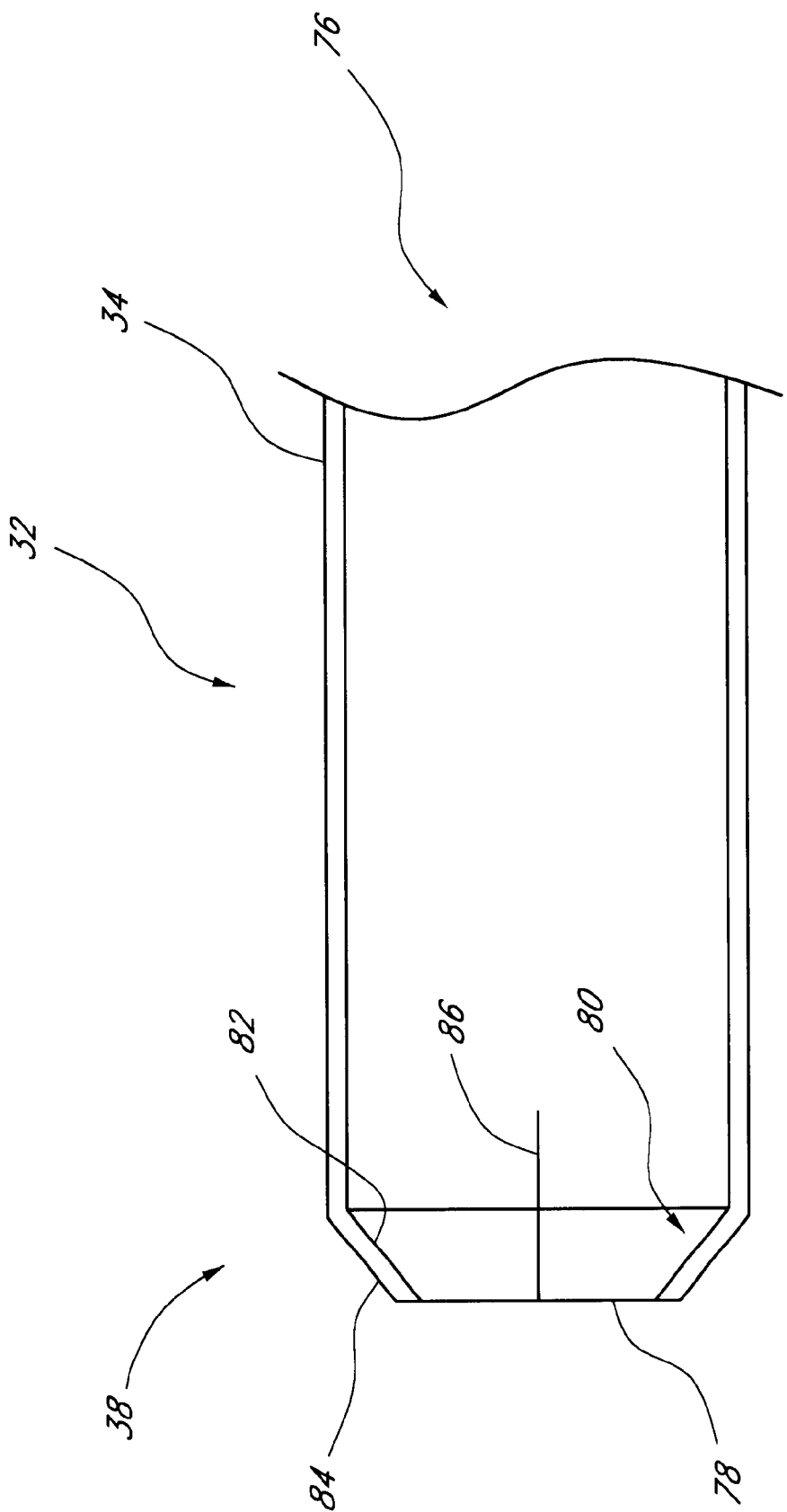

Referring to FIG. 4A, there is disclosed an enlarged distal end 38 of sleeve 32 including a seed retention structure to prevent inadvertent loss of seeds from the sleeve 32. Central lumen 76 within sleeve 32 is in communication with a distal opening 78, for deploying radioactive seeds and spacers or other material. At least one retention structure 80 is provided, for resisting accidental distal loss of the radioactive seeds 70 or spacers 72. In the illustrated embodiment, the retention structure 80 comprises one or more interference surfaces 82. Interference surfaces 82 are movably positioned at least part way across the path of the load to retain the load within the central lumen 76. The interference surface 82 is movable so that it can be advanced from a first position in which it obstructs the load to a second position in which the load may be distally deployed through the distal opening 78. Preferably, the interference surface 82 is biased in the direction of the first position.

In this manner, a seed may be forcibly advanced through the distal opening 78 by pushing the interference surface 82 out of the way. Once the seed has been deployed from the distal opening 78, the interference surface 82 returns to its first position, thereby providing tactile feedback to the clinician that the seed has been deployed and resisting accidental deployment of subsequent radioactive seeds or spacers.

The interference surface 82 may be provided on any of a variety of structures, such as radially inwardly extending tabs, flanges, tapered surfaces, inserts or other interference elements, as will be apparent to those of skill in the art in view of the disclosure herein. The interference surface 82 may be integrally formed with the sleeve 32, or may be manufactured separately and attached to the tubular body 34 during the manufacture process.

In the illustrated embodiment, the interference surface 82 is provided on the radially inwardly facing surface of an inclined flange 84. The illustrate flange 84 is in the form of an annular frusto-conical tip on the tubular body 34, inclining radially inwardly in the distal direction. Preferably, one or more axially extending slots 86 extend from the distal limit of the inclined flange 84, in a proximal direction, to facilitate the enlargement of the distal opening 78 when the clinician puts sufficient distal pressure on the obturator hub 50 to deploy a seed or spacer.

The interference surface 82, whether carried by inclined flange 84 or other structure, can extend circumferentially either entirely around or only part way around the distal opening 78. For example, in the embodiment illustrated in FIG. 4A, the inclined flange 84 extends substantially the entire circumference of the distal opening 78. Alternatively, inclined flange 84 may extend no more than about 180°, no more than about 90°, or even no more than about 10° or 15° of the circumference of distal opening 78. The foregoing circumferential lengths of inclined flange 84 may represent a single continuous flange, or the sum of a plurality of distally inclined tabs. For example, by removing portions of the flange, a plurality of spaced apart tabs may be provided such as two or four or six or more tabs, spaced apart around the circumference of distal opening 78. The number and spacing of these tabs can be selected to achieve a desired minimum deployment force and tactile feedback as will be apparent to those of skill in the art in view of the disclosure therein.

The illustrated inclined flange 84 can be manufactured in any of a variety of ways, depending in part upon the material of tubular body 34. For example, molding, machining, or attachment of a separately formed tip such as with adhesives, thermal bonding or other technique may be used. In one embodiment, the flange 84 is formed in a polyimide tubular body 34 by advancing the tube into a frusto-conical bore with a corresponding mandrel positioned within central lumen 76, under the application of heat.

An alternate retention structure 80 is illustrated in FIG. 4B. An inclined tab 88 is created by forming a slot 90 in a generally U-shaped configuration, or by forming two parallel slots 90 at the distal end of the tubular body 34. The resulting tab 88 may then be bent radially inwardly to provide an interference surface 82 in the path of the brachytherapy seed. One or two or more inclined tabs 88 may be provided in a common plane transverse to the longitudinal axis of the tube 34, depending upon the desired performance characteristics of the device.

A similar structure may be provided at the proximal end of the deployable load 60, if desired, to prevent proximal loss or travel of seeds 70 or spacers 72. The proximal stop 92 may be formed by a slot 94 in the wall of the tubular body 34, such as in a U- or V-shape. The resulting proximal stop 92 may be bent radially inwardly to provide a ramp 98 and a stop surface 96. As will be apparent to those of skill in the art, ramp 98 allows distal advancement of seeds through the central lumen 78 but proximal travel of seeds will be prevented by stop surface 96.

The provision of a proximal stop 92 is optional, and may be desirable in embodiments in which shipping of loaded sleeves is accomplished without an obturator 42 positioned within the tubular body 34 proximally of the deployable load 60.

Figure 4C:
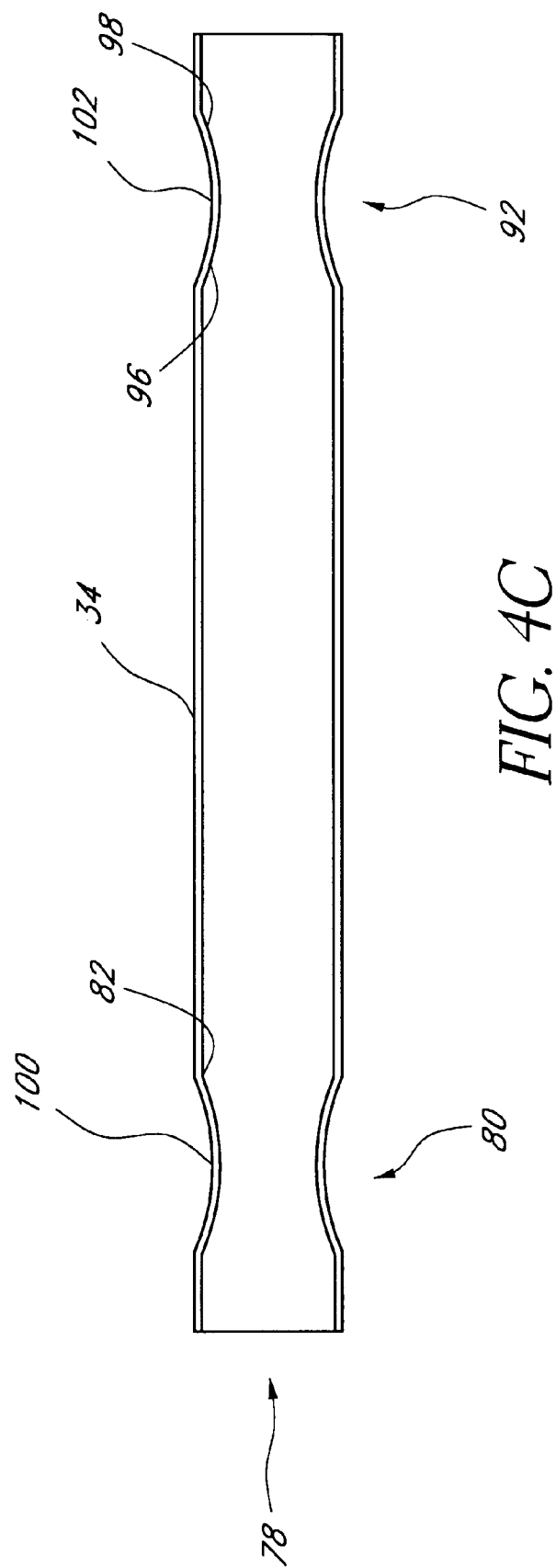

Referring to FIG. 4C, there is illustrated an alternate retention structure 80 and optional proximal stop 92. Retention structure 80 is formed by a crimp or dent 100 in the wall 34 of tubular body 32. The crimp 100 provides an interference surface 82, which interferes with the distal travel of a brachytherapy seed 70 or spacer 72. Upon application of sufficient distal force on the brachytherapy seed 70, the interference surface 82 is pushed out of the path of travel such that the seed 70 is deployed through the distal opening 78. Crimp 100 may be in the form of an annular indentation, or one or more discrete indentations or dents around the circumference of the tubular body 34. For example, two opposing crimps may be provided or three crimps provided with 120° spacing, or four crimps at 90° spacing around the circumference of the tubular body 34. The precise location, depth, and number of crimps 100 may be determined through routine experimentation, depending upon the desired performance of the device.

Similarly, the optimal proximal stop 92 is provided by one or more crimps or dents 102. The resulting structure provides a ramp 98 to permit distal travel of radioactive seeds 70 under distal pressure by an obturator or other loading device. The stop surface 96 inhibits proximal travel of the seeds or spacers.

The crimp 100 or 102 may be provided in any of a variety of manners depending upon the construction materials and wall thickness of the tubular body 34. For example, certain materials may retain a crimp provided by controlled mechanical compression of the tubular body 34. The compression may be accomplished with or without the application of heat, depending upon the material and wall thickness. In one embodiment in which the tubular body 34 comprises a polyimide extrusion, the crimp 100 and, optionally, crimp 102 is provided by compressing the wall 34 at an elevated temperature within the range of from about 600° F. to about 800° F.

Figure 4D:
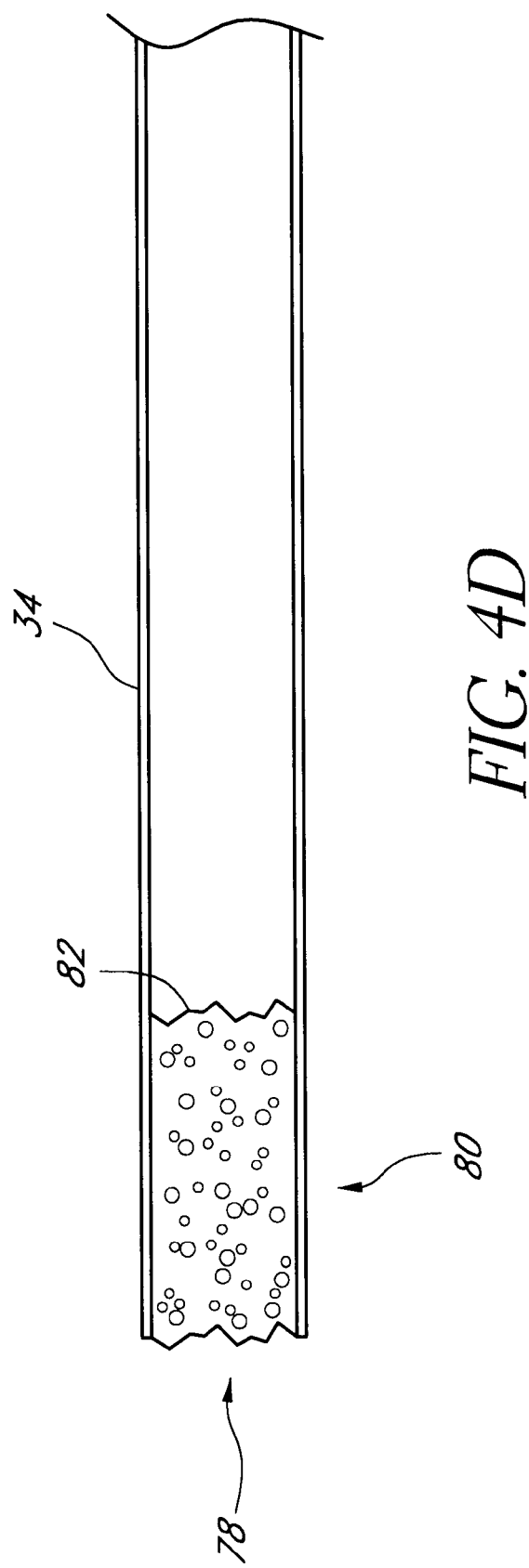

An alternate retention technique is schematically illustrated in FIG. 4D. In this embodiment, the distal opening 78 is obstructed by a removable plug such as a wax or gel. Suitable materials for the plug include medical grade bonewax, available from medical goods suppliers. Care should be taken to ensure consistent needle to needle plug size, so that the seeds may be precisely placed at the treatment site.

Referring to FIG. 5A, there is illustrated a cross-sectional view through a sleeve hub 40, for connecting to the proximal end 36 of sleeve 32. In general, sleeve hub 40 comprises a proximal connector 106 such as a standard luer connector or a simple annular flange. The distal end 108 of sleeve hub 40 is provided with a lumen or bore 104 for receiving the proximal end 36 of sleeve 32. Sleeve 32 is preferably advanced into lumen 104 during the manufacturing process and secured in any of a variety of ways such as through the use of adhesives, solvent bonding, thermal bonding, or other techniques known in the medical device manufacturing arts.

A proximally extending annular recess 110 defines a distal projection or nose 112, which may serve as the male component of a luer connector. For this purpose, the wall of annular recess 110 may be provided with radially inwardly directed threads as are well understood in the art. In this manner, the hub 40 may be advanced distally toward and connected to the hub 30 by a partial rotation of hub 40 with respect to hub 30. A gripping surface 114 may be provided on the hub 40, including friction enhancing surface structures such as a plurality of axially extending ribs as is understood in the art. Preferably, the hub 40 is in the form of a male luer connector which may be securely engaged with a complementary female luer connector on hub 30 of the needle 22. In particular, the projection 112 is provided with a tapered surface 116, which fits within a complimentary tapered surface 118 surrounding a cavity in the proximal end of hub 30.

Brachytherapy needles 22 are currently marketed by more than one manufacturer, and complete uniformity in the design of hub 30 has not been achieved. The taper angle on interior surface 118 on the needle hub 30 is not uniform for all manufacturers. For example, some needles 22 are available having a taper on surface 118 of about 6 degrees, while other commonly available commercial needles 22 have a taper angle on surface 118 of about 2 degrees. If the taper angle on surface 118 does not correspond closely to the taper angle on surface 116, a secure fit between the needle 22 and sleeve 32 will not be achieved.

Accordingly, referring to FIG. 5B, there is provided in accordance with another aspect of the present invention a universal hub 40 for attachment to the proximal end 36 of tubular body 34. The projection 112 is provided with a first taper zone 120 having a first taper angle, and a second, distal taper zone 122 having a second, greater taper angle. The projection 112 on hub 40 can thus accommodate needle hubs 30 of differing internal tapers on surface 118. In one embodiment, the tapered surface 120 extends at an angle of approximately 2 degrees with respect to the longitudinal axis of tubular body 34, and tapered surface 122 resides at an angle of approximately 6 degrees with respect to the longitudinal axis of tubular body 34. Alternative tapers may readily be selected, depending upon the construction of the corresponding needle hubs which are desirably accommodated. In addition, three or more distinct taper surfaces may be provided on projection 112, if desired to accommodate a larger number of corresponding needle hubs.

Figure 6:
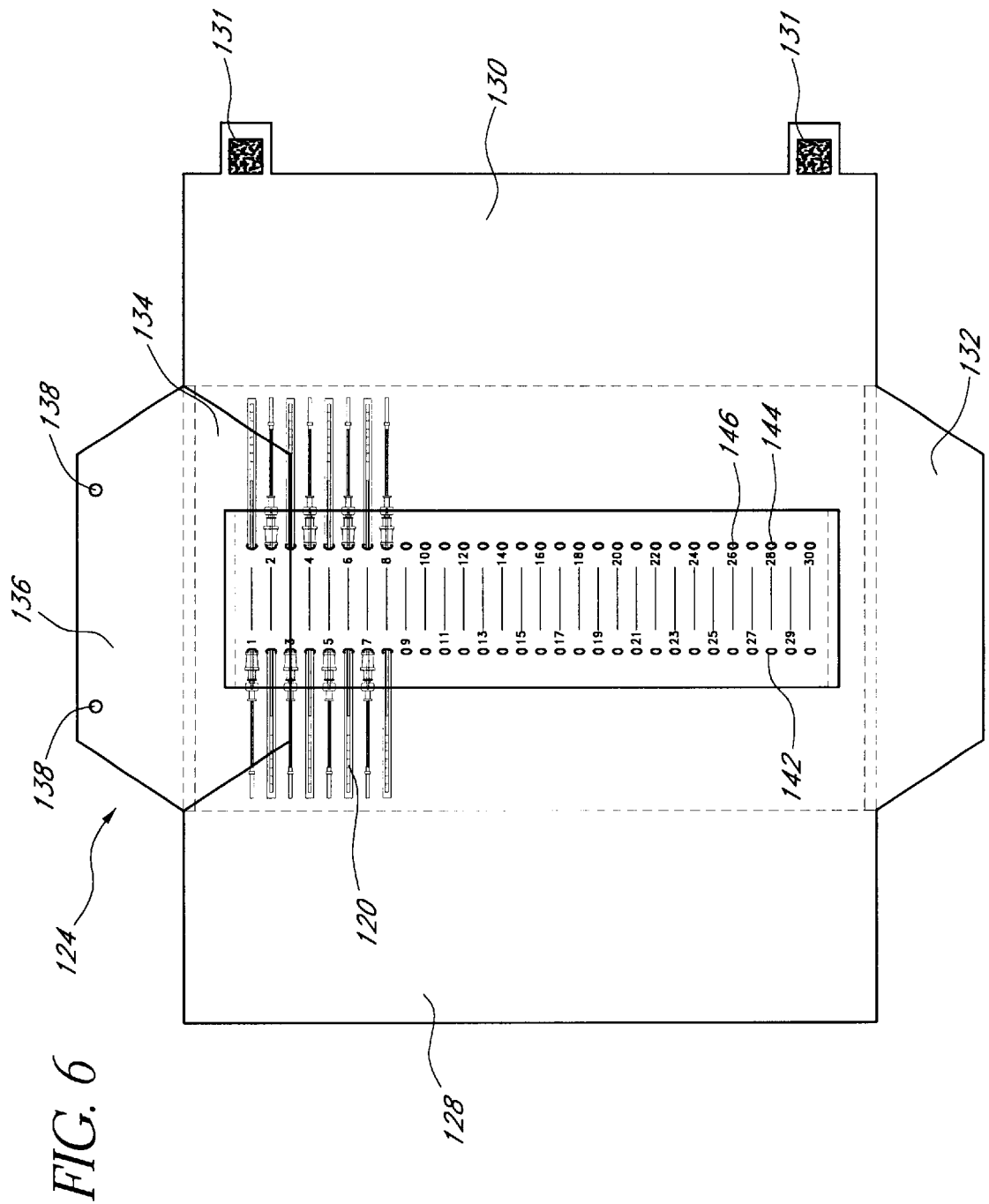
FIG. 6 is a schematic view of needles, pre-loaded sleeves, and obturators organized on a needle drape.

Referring to FIG. 6, there is illustrated a schematic plan view of a drape 124 in accordance with the present invention, adapted to carry a plurality of brachytherapy seed deployment devices 20. The drape 124 comprises a back portion 126, a left flap 128 and a right flap 130 for folding over the brachytherapy seed deployment devices 20. Alternatively, a single flap may be utilized to cover the entire front surface of the drape 124. The right flap 130 in the illustrated embodiment is provided with at least one removable attachment structure such as an adhesive patch 131. Adhesive patch 131 may be removably attached to the back surface of left flap 128 to releasably close the drape 124.

The illustrated drape 124 is additionally provided with a bottom flap 132 and a top flap 134. A support 136 is preferably provided with one or more attachment structures such as apertures 138, for attaching the drape 124 to a support structure as will be described.

The drape 124 is preferably additionally provided with a needle carrier 140. In the illustrated embodiment, needle carrier 140 is secured to the back 126, such that it will be covered by the closed right and left flaps 130 and 128. Needle carrier 140 is provided with a plurality of pairs of opposing apertures such as 142 and 144 adapted to receive a brachytherapy seed deployment device 20 therethrough. Although 30 opposing pairs of apertures are illustrated in FIG. 6, the capacity of the needle carrier 140 may be varied as desired. Preferably, each opposing pair of apertures 142 and 144 is provided with an identifying indicium 146 such as a letter or number to allow identification of each unique deployment device 20.

The drape 124 may be manufactured in any of a variety of ways, such as by cutting a desired profile on a polymeric sheet comprising any of a variety of medical grade, sterilizable materials. Suitable materials include polypropylene. In one embodiment, the back portion 126 has a vertical dimension of about 18 inches and a horizontal dimension of about 14.5 inches. The width in the horizontal direction of each of the left flap 128 and right flap 130 from the fold to the outer edge is approximately 7.75 inches. The needle carrier 140 comprises polypropylene, and is heat sealed at the top and bottom edges to the back 126. The back portion 126 or other portion of the drape 124 may optionally be additionally provided with a radiation attenuation layer such as a thin lead sheet to contribute to the radiation attenuation function of the needle pig 152 as will be discussed.

FIGS. 7A and 7B illustrate pages 1 and 2 of a needle loading report, which will accompany the loaded drape 124. On page 1 of the needle loading report illustrated at FIG. 7A, the spatial orientation of each needle at the treatment site is identified, as well as the number of radioactive seeds per needle. Page 2 of the needle loading report illustrated at FIG. 7B discloses the precise seed and spacer arrangement for each needle contained in the drape 124. Additional patient information is also included. In accordance with the present invention, each of the needles is preloaded at the point of manufacture for a unique patient's needs, and delivered to the treatment site. The clinical staff receive the loaded drape 124 and corresponding needle report, which enables them to both identify the precise desired location of each needle as well as audit the contents of each needle compared to the desired needle loading report, due to the transparent wall of the tubular sleeve 32.

Figure 8:
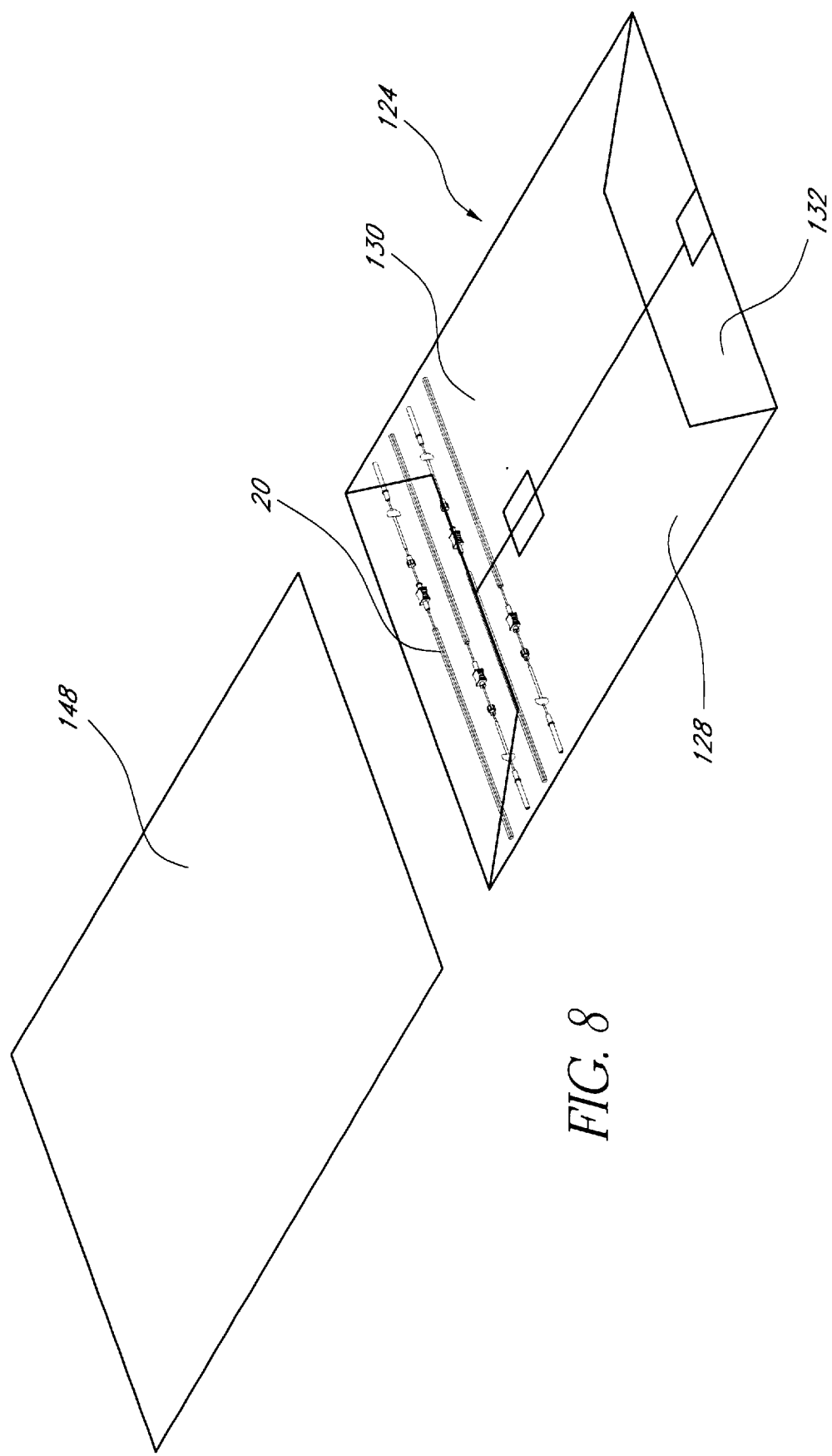
FIG. 8 is an exploded perspective view of a folded needle drape, and an outer pouch.

FIG. 8 illustrates a needle drape 124 including four brachytherapy seed deployment devices 20, in which the left flap 128, right flap 130, and bottom flap 132 are folded closed. For shipping, the entire folded needle drape is positioned within a sterile pouch 148.

Figure 9:
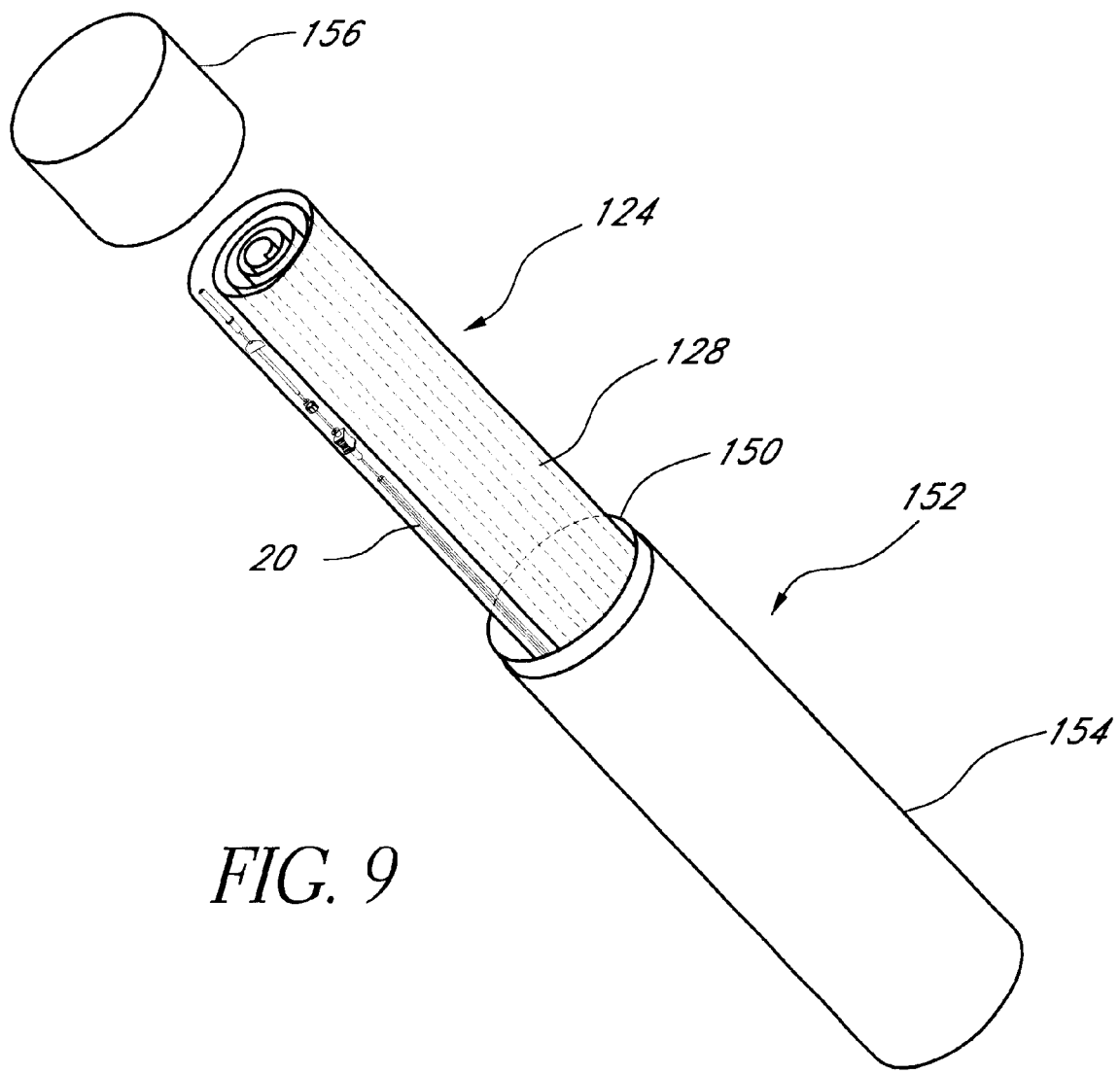
FIG. 9 is a partially exploded perspective view of a needle drape, pouch, needle canister lid and needle canister base.

Referring to FIG. 9, the pouch 148 containing the needle drape 124 is rolled following the loading process and positioned within a chamber 150 in a needle pig 152. The needle pig 152 comprises a needle canister base 154 having the chamber 150 therein, together with a corresponding needle canister lid 156. Preferably, the needle canister base 154 and lid 156 are made from lead, or other material which helps attenuate radiation from the brachytherapy seeds.

Figure 10:
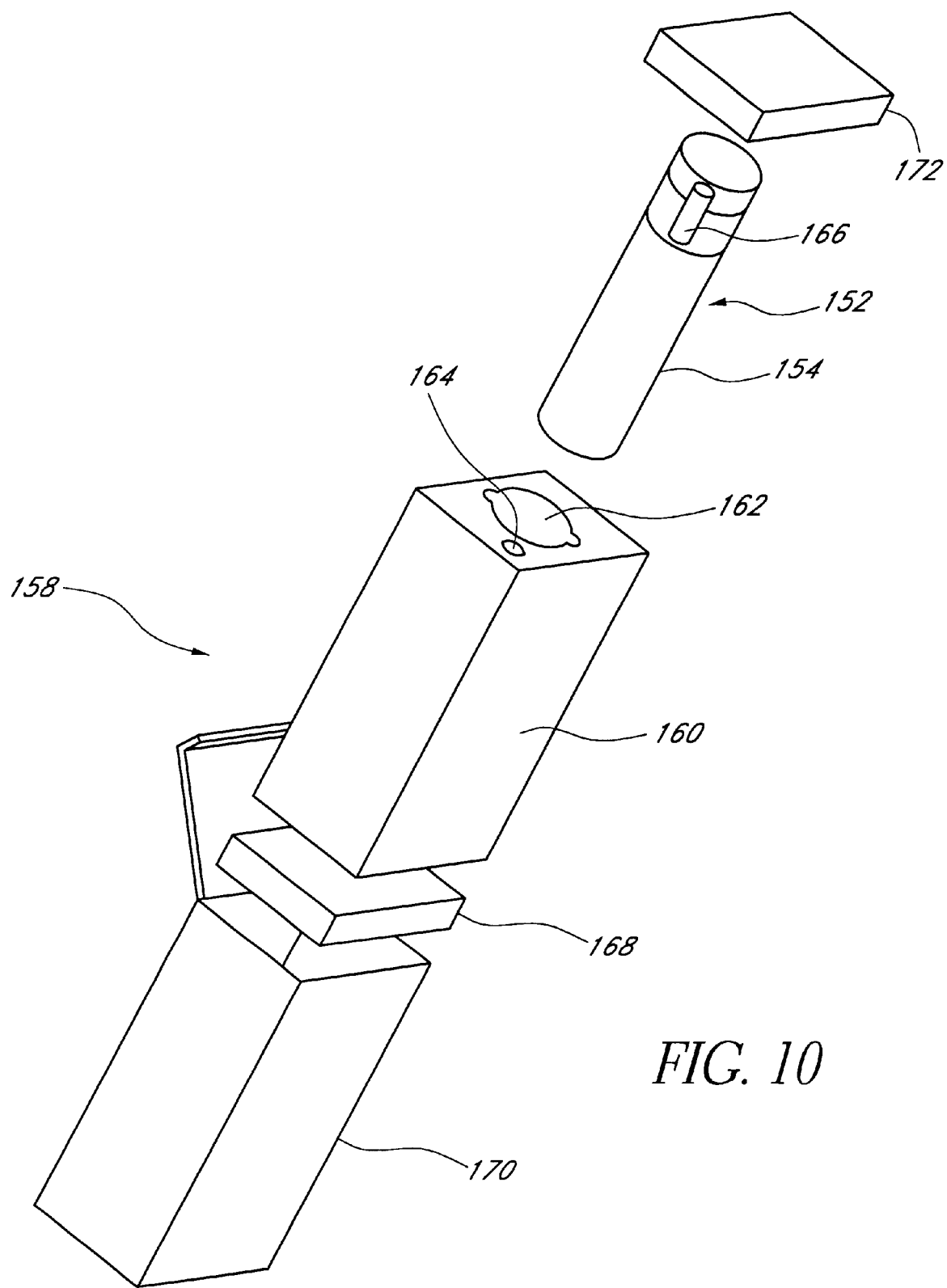
FIG. 10 is an exploded perspective view of a shipping assembly.

Referring to FIG. 10, a shipping assembly 158 is illustrated for shipment of the needle pig 152 to the clinical site. In the illustrated embodiment, a foam or other support 160 is provided with a needle pig cavity 162 for removably received the needle pig 152. A calibration pig cavity 164 is also provided, for receiving a calibration seed pig 166 which will be described below. The support 160, optionally with an additional foam base 168 is positioned within a shipping box 170. A foam lid 172 or other cushioning or closure element is positioned on top of the calibration seed pig 166 and needle pig 152, and placed within the box 170. The various components of the shipping assembly 158 preferably sufficiently attenuate radiation from the brachytherapy seeds that the loaded shipping assembly 158 may be transported under ordinary shipping conditions such as via Federal Express or other commercial carrier.

Figure 11:
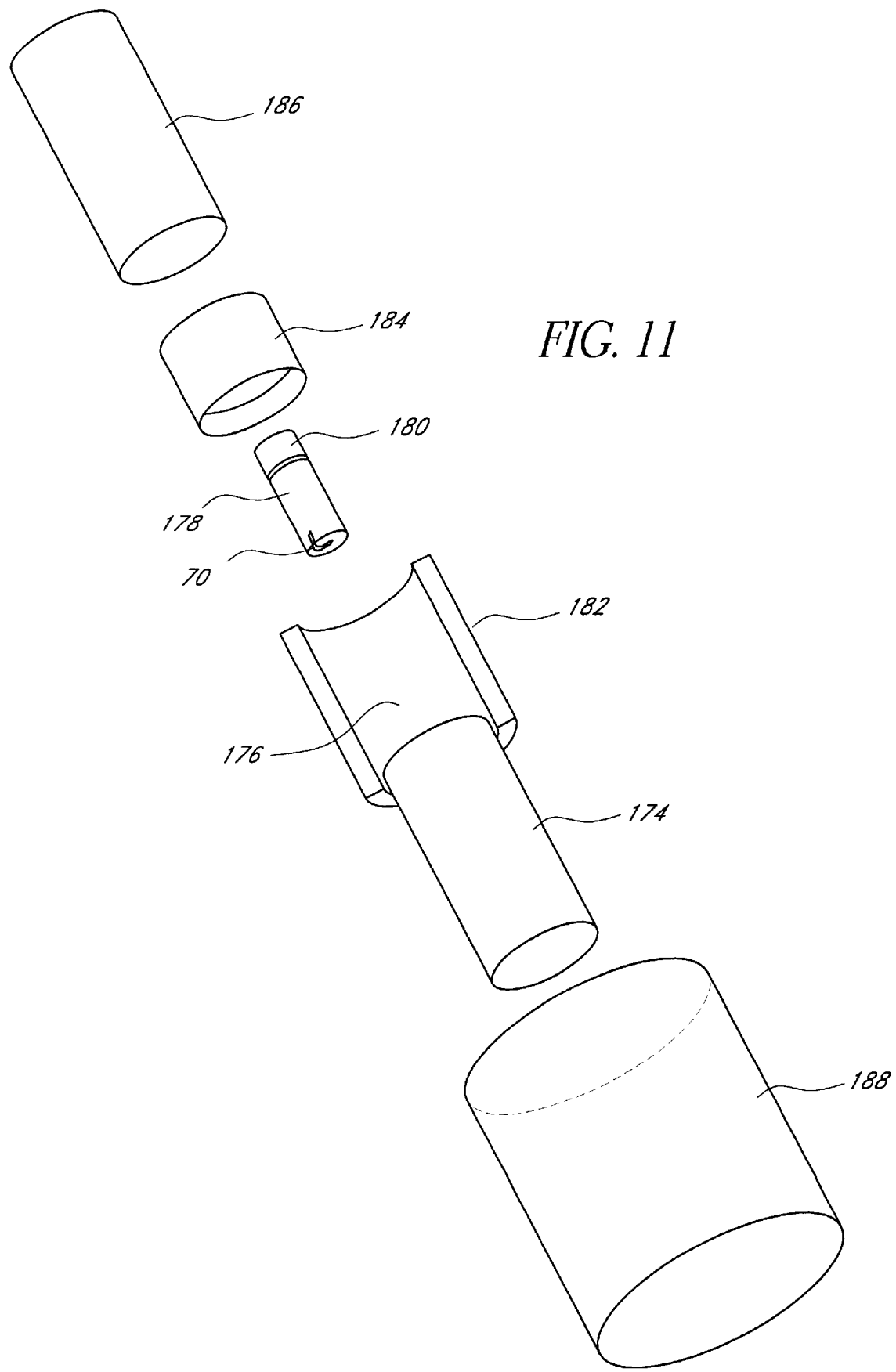
FIG. 11 is an exploded perspective view of a calibration seed pig.

Referring to FIG. 11, there is illustrated an exploded view of an exemplary calibration seed pig 166. Due to the known characteristics of radioactive decay, the activity of the brachytherapy seeds 70 is constantly declining until the radiation has dropped below a therapeutically useful range, and ultimately becomes fully dissipated. As a consequence, the activity must be assayed or calibrated at the time of the clinical procedure, to enable delivery of the desired radioactive dose. This is accomplished in the context of the present brachytherapy system by providing a calibration seed pig 166 which includes brachytherapy seeds 70 of the same activity as the seeds 70 which have been preloaded into each of the brachytherapy seed deployment devices 20. The provision of extra calibration seeds in the separate calibration seed pig 166 enables the clinical staff to calibrate the activity of the seeds without needing to disassemble any of the preloaded deployment devices or break the sterile seal on the needle pig 152.

The calibration seed pig 166 includes a pig base 174, constructed from a suitable radiation attenuating material such as lead. The pig base 174 is provided with a cavity 176 for receiving a glass vial 178. Glass vial 178 includes a plurality of seeds 70 having the same activity as the corresponding seeds in the associated deployment devices. A lid 180 is provided for the glass vial 178. The glass vial 178 is positioned within the cavity 176. The cavity 176 may be lined by an annular foam insert 182, to provide additional cushioning for the glass vial 178. The pig base 174 is closed by a corresponding pig lid 184. Preferably, a label 186 is provided on the pig base 174, and may be held thereto by an outer layer of shrink wrap 188.

Any of a variety of alternate constructions for the calibration seed pig may be devised, in view of the disclosure herein, to achieve the advantages of the present invention. In general, the distinct calibration seed pig enables the calibration of the brachytherapy seed deployment system without needing to open the sterile drape which includes the deployment device.

Figure 12:
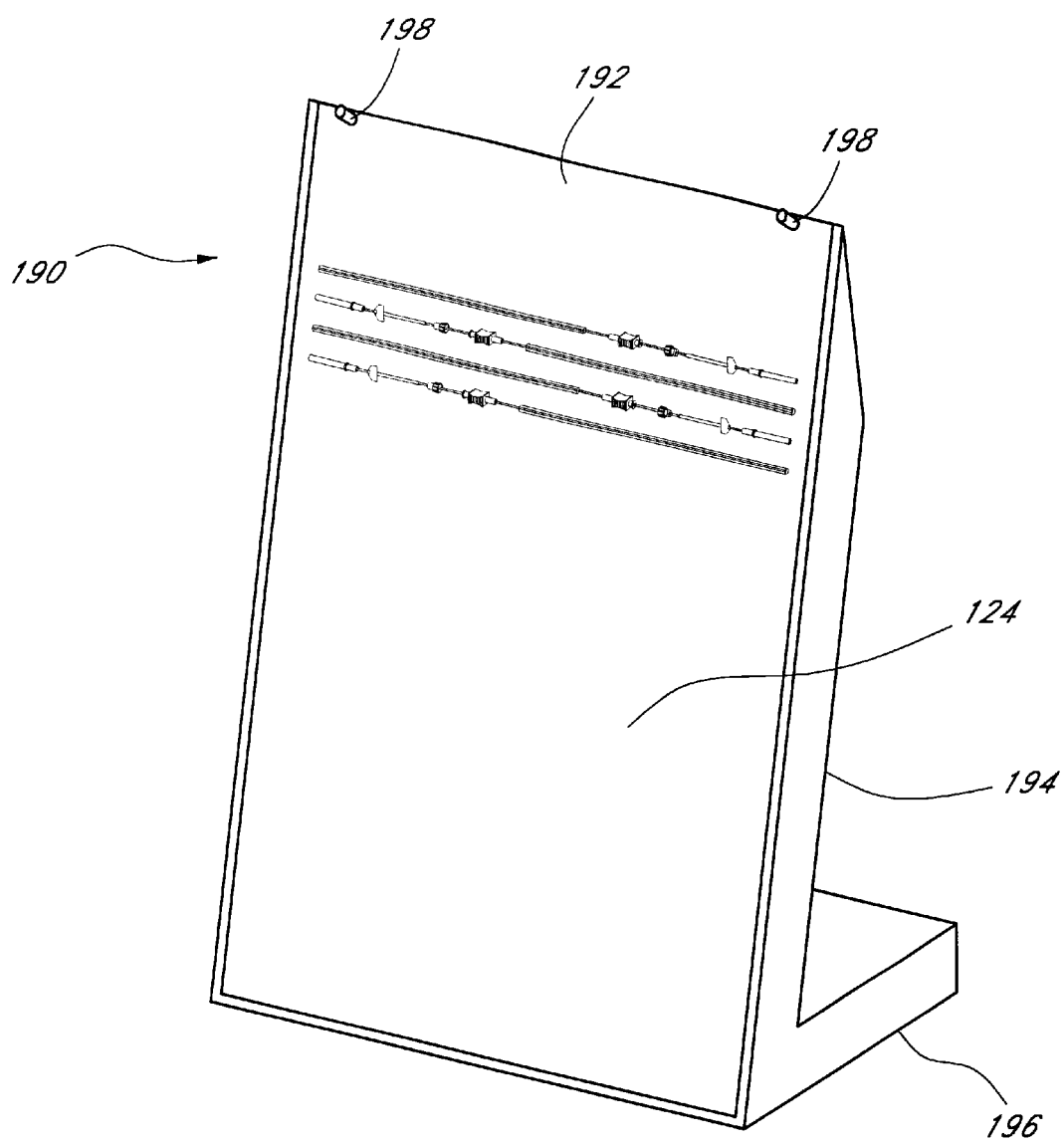
FIG. 12 is a front elevational perspective view of a closed needle drape attached to a needle stand.
Figure 13:
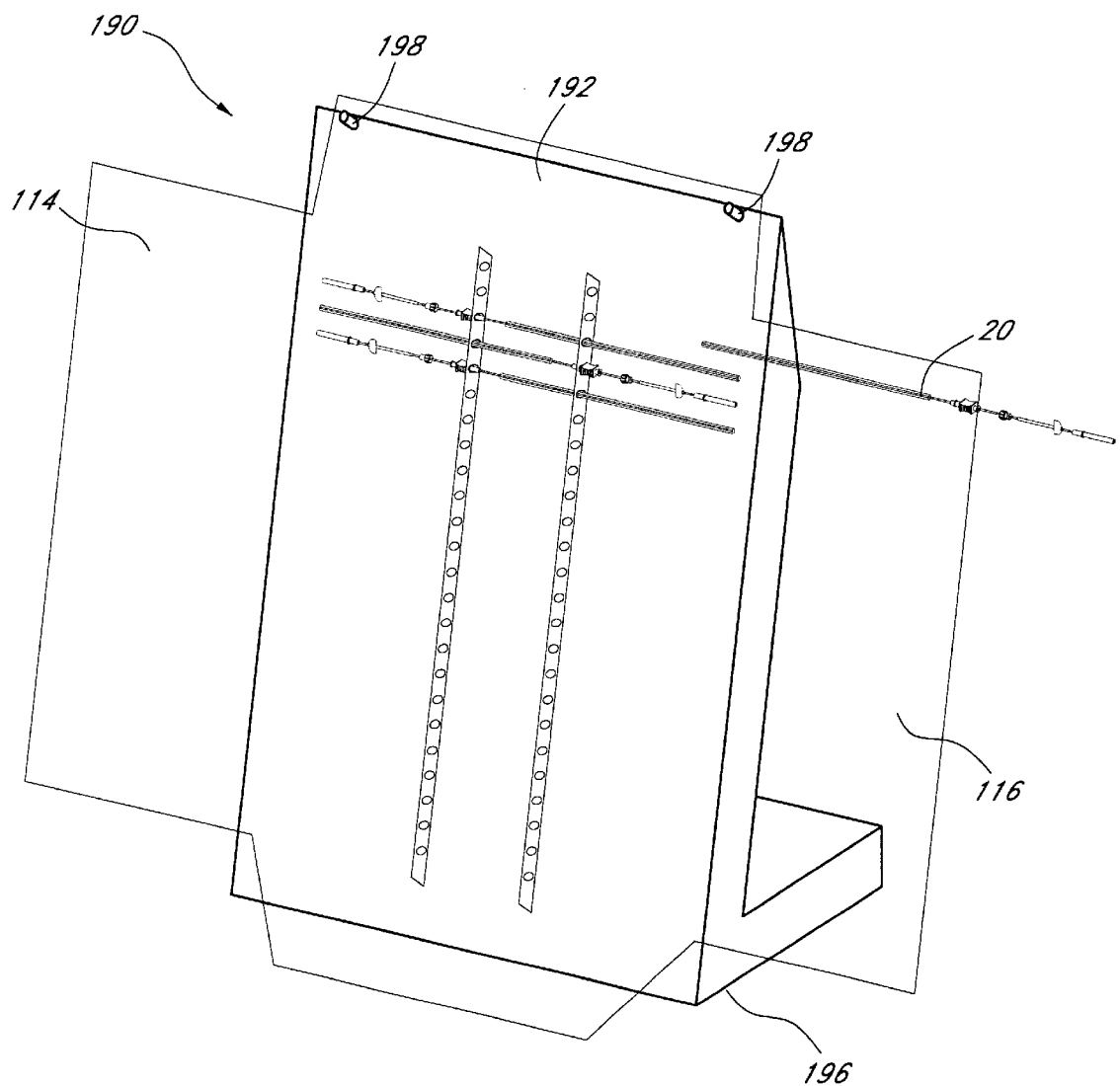
FIG. 13 is a view of a needle drape attached to a needle stand as in FIG. 11, with the needle drape open.

Referring to FIGS. 12 and 13, there is illustrated a drape stand 190 in accordance with another aspect of the brachytherapy seed delivery system of the present invention. The drape stand 190 comprises a support surface 192 for supporting a drape 124. Preferably, the support surface 192 lies in a plane which is inclined with respect to the horizontal, such as within the range of from about 45° to about 90°. Alternatively, the support surface 192 can be parallel to horizontal, although this orientation will require a greater countertop surface area.

The support surface 192 may be supported by or attached to a frame 194, and a base 196. Preferably, the base 196 is designed to fit on an existing surgical table, and has dimensions of approximately 9 inches by about 14 inches. The support surface 192 is preferably additionally provided with one or two or more attachment structures 198, such as post or clips for retaining a drape 124 thereon. In the illustrated embodiment, first and second posts 198 are adapted to receive first and second apertures 138 (see FIG. 6) to retain the drape 124 thereon.

As illustrated in FIG. 13, the right and left flaps 130 and 128 of the drape 124 may be opened, while the drape 124 is secured to the support surface 192, to facilitate sequential removal of each brachytherapy seed deployment device 20 as it may be needed during the procedure.

The drape stand 190 may be manufactured either as a one-time use disposable device, or as a reusable device. Preferably, the drape stand 190 is reusable, and may be manufactured from any other variety of materials such as stainless steel, or plastics which are well known in the medical device arts.

In addition to other advantages discussed previously herein, two types of customized dosing profiles are facilitated by the present invention. In the first, seed to seed activity may be varied within a single sleeve 32, to achieve higher resolution dosing patterns compared to the standard uniform seed activity devices currently in use. For example, at least a first seed within a sleeve 32 may be provided with a first activity, and at least a second seed in the same sleeve may be provided with a second, different activity. By "different", the inventors contemplate a measurable, intended different activity, and not merely manufacturing tolerance differences. Two or more seeds may be provided at the first activity, and two or more seeds may be provided at the second activity. Additional combinations may also be provided, based upon patient needs. In addition, more than two different activities may be provided in a single sleeve 32. For example, at least a first seed may be provided at a first activity, at least a second seed at a second activity, and at least a third seed at a third activity within a single sleeve 32.

In this manner, the activity and resulting delivered dose can be controllably varied along the axial direction of the needle. One or more needles prepared in this manner will have a first zone which exhibits at least a first activity, and a second zone which exhibits at least a second, different activity.

A second form of dose customization that can be readily accomplished in accordance with the present invention results from needle to needle variations in activity. A first sleeve 32 may be provided with one or more seeds having a first activity, and a second sleeve 32 may be provided with one or more seeds having a second, different activity. Combinations of the two forms of dose customization can also be used to optimize conformity between the three dimensional delivered dose profile and the desired treatment site.

Once the three dimensional shape of the desired target tissue has been established for a particular patient, and tissue to be avoided (e.g., urethra, rectum) has been mapped, the sleeves are loaded with seeds and spacers in a pattern to most closely conform to the target tissue in both the axial dimension and the transverse (to the axis of the needles) dimension. The deployment devices are assembled and loaded into the drape and prepared for shipment to the clinical site. At the site, the drape is preferably placed on a drape stand and each needle is removed and advanced into the target tissue at its unique, predetermined site to produce the predetermined three dimensional dosing profile. Preprocedure calibration can be enabled by either providing calibration seeds at each activity level, or providing calibration seeds at a single level or two levels from which calibration values for the other levels can be extrapolated.

Although exemplary embodiments of the invention have been shown and described, many changes, modifications and substitutions may be made by one having ordinary skill in the art without necessarily departing from the spirit and scope of this invention.

What is claimed is:

1. A brachytherapy system, comprising:
   an elongate, tubular needle;
   an elongate tubular sleeve, positioned within the needle, the sleeve having a proximal end and a distal end;
   at least one brachytherapy seed in the sleeve;
   an obturator extending into the proximal end of the sleeve; and
   a flexible drape;
   wherein the needle is carried by the drape.

2. A brachytherapy system as in claim 1, comprising a plurality of brachytherapy seeds and spacers within the sleeve.

3. A brachytherapy system as in claim 1, comprising a plurality of needles carried by the drape.

4. A brachytherapy system as in claim 1, wherein the drape is positioned within a pig.

5. A brachytherapy system as in claim 1, further comprising a plurality of calibration seeds.

6. A brachytherapy system as in claim 5, wherein the calibration seeds are carried by a calibration seed pig.

7. A brachytherapy system as in claim 4, comprising a plurality of needles carried by the drape, wherein the drape is rolled about an axis which is parallel to the axis of the needles and positioned within the pig.

8. A brachytherapy system as in claim 1, further comprising a lock for preventing inadvertent distal advancement of the obturator into the sleeve.

9. A brachytherapy system, comprising:
   a shipping container;
   a needle pig in the shipping container;
   a calibration seed pig in the shipping container;
   a plurality of brachytherapy needles in the needle pig, the brachytherapy needles preloaded with brachytherapy seeds and spacers; and
   at least one calibration seed in the calibration pig;
   wherein the calibration seed can be accessed without opening the needle pig.

10. A brachytherapy system as in claim 9, wherein the brachytherapy needles are carried by a flexible drape.

11. A brachytherapy system as in claim 9, further comprising a needle loading report in the container.

12. A brachytherapy system as in claim 9, wherein each brachytherapy needle carries a tubular sleeve, and brachytherapy seeds are carried within the sleeve.

13. A brachytherapy system as in claim 12, wherein each sleeve is visually transparent.

14. A brachytherapy system as in claim 12, wherein each sleeve further comprises a retention structure for retaining seeds and spacers therein.

15. A brachytherapy system as in claim 12, further comprising an obturator positioned part way within each sleeve.

16. A nonuniform dosing profile brachytherapy needle set, comprising:
   a flexible drape;
   a plurality of needles, each containing at least one brachytherapy seed, the needles carried by the drape;
   at least a first seed in a first needle having a first activity; and
   at least a second seed in a second needle having a second, different activity.

* * * * *